(12) United States Patent
Chen

(10) Patent No.: US 6,939,863 B2
(45) Date of Patent: Sep. 6, 2005

(54) PREVENTION OF ATHEROSCLEROSIS AND RESTENOSIS

(76) Inventor: Wei-Jan Chen, 10 F, No. 15 Da- Chi Street, Taipei (TW)

( * ) Notice: Subject to any disclaimer, the term of this patent is extended or adjusted under 35 U.S.C. 154(b) by 0 days.

(21) Appl. No.: 10/273,057

(22) Filed: Oct. 16, 2002

(65) Prior Publication Data

US 2003/0130228 A1 Jul. 10, 2003

Related U.S. Application Data

(60) Provisional application No. 60/345,766, filed on Jan. 4, 2002.

(30) Foreign Application Priority Data

Jun. 21, 2002 (CN) ......................... 91113579 A

(51) Int. Cl.$^7$ .......................... A61N 43/04; A61K 31/70
(52) U.S. Cl. .......................... 514/50; 424/423
(58) Field of Search ............................ 514/50; 424/423

(56) References Cited

U.S. PATENT DOCUMENTS

| | | | |
|---|---|---|---|
| 5,310,742 A | | 5/1994 | Elias et al. |
| 5,571,523 A | * | 11/1996 | Lee et al. .................... 424/423 |
| 5,773,029 A | | 6/1998 | Chiesi et al. |
| 5,821,260 A | | 10/1998 | Medford et al. |
| 6,096,753 A | | 8/2000 | Spohr et al. |
| 6,365,616 B1 | | 4/2002 | Kohn et al. |
| 2002/0022022 A1 | | 2/2002 | Shi et al. |
| 2002/0025979 A1 | | 2/2002 | Kunz et al. |

FOREIGN PATENT DOCUMENTS

| | | | |
|---|---|---|---|
| WO | 96/28114 | | 9/1996 |
| WO | WO 96/28114 | * | 9/1996 |
| WO | 00/10980 | | 3/2000 |
| WO | 01/60805 | | 8/2001 |

OTHER PUBLICATIONS

Bennett et al., "Vascular Smooth Muscle Cell Apoptosis—A Dangerous Phenomenon in Vascular Disease?", Journal of Clinica and Basic Cardiology, vol. 3, issue 1, 2000, pp. 63–65.*
Lee et al., Exp. Cell. Res. 239(2):447–453 (1998), Synchronization of cultured vascular smooth muscle cells following reversal of quiescence induced by treatment with the antioxidanyt N–acetylcysteine.
Tsai et al., J. Biol. Chem., 271:3667–3670 (1996). Induction of apoptosis by pyrrolidiniedithiocarbamate and N–acetylcysteine in vascular smooth muscle cells.
Ialenti et al., Naunyn Schmiedeberg's Arch. Pharmacol., 364(4):343–350 (2001), Role of nuclear factor–kB in a rat model of vascular injury.
Cao et al., Biochem. Biophys. Res. Comm., 292(1):50–57 (2002), Chemical induction of cellular antioxidants affords marked protection against oxidative injury in vascular smooth muscle cells.

Hicks et al., Biochem, Pharmacol., 43(3):439–444 (1992), Antioxidant activity of proplthiouracil.
Faure et al., Chem. Biol. Interact., 77:173–185 (1991), Evaluation of the antioxidant properties of thyroid hormones and propylthiouracil in the brain–homogenate autoxidation system and in the free radical–mediated oxidation of erythrocyte membranes.
Grieve et al., Brit. J. Pharmacol., 127(1):1–8 (1999), Effects of oral propylthiouracil treatment on nitric oxide production in rat aorta.
Adali et al., Clin. Biochem., 32(5):363–367 (1999), Effects of propylthiouracil, propranolo, and vitamin E on lipid peroxidation and antioxidant status in hyperthyroid patients.
Giuriato et al., Arteriscler. Thromb., 11(5):1376–89 (1991), Aortic intimal thickening and myosin isoform expression in hyperthyroid rabbits.
Finking et al., Atherosclerosis, 135:1–7 (1997), Nikolaj Nikolajewitsch Anitshcokow (1885–1964) established the cholesterol–fed rabbit as a model for atherosclerosis research.
Johnson et al., Thromb. Haemost., 81:835–843 (1999), Scientific and Standardization Committee Communication. The utility of animal models in the preclinical study of interventions to prevent human coronary artery restenosis: analysis and recommendations. On behalf of the Subcommittee on Animal, Cellular, and Molecular Models of Throbosis and Haimostasis of the Scientific and Standardization Committee of the International Society on Thrombosis and Haemostasis.
Narayanaswamy et al., J. Vasc. Interv. Radiol., 11:5–17 (2000), State of the art: Animal models for atherosclerosis, restenosis, and endovascular graft research.
Ross et al. J Pharmacol Exp Therapeutics 285:1233–1238 (1998), Effect of Antithyroid Drugs on Hdroxyl Radical Formation and α–1–Proteinase Inhibitor Inactivation by Neutrophils: Therapeutic Implications.
Freyschuss et al, J Clin Invest 91:1282 (1993), Antioxidant Treatment Inhibits the Development of Intimal Thickening after Balloon Injury of the Aorta in Hypercholesterolemic Rabbits.

(Continued)

Primary Examiner—James O. Wilson
Assistant Examiner—Traviss C. McIntosh, III
(74) Attorney, Agent, or Firm—David R Preston & Associates; David Preston

(57) ABSTRACT

The present application concerns pharmaceutical compositions, methods of use thereof and medical devices for preventing or treating atheroscrosiss or restenosis or both. The present invention discloses a pharmaceutical composition, including a pharmaceutically acceptable carrier and PTU in an amount sufficient to prevent atherosclerosis or restenosis in a subject. The present invention further discloses a method of inhibiting atherosclerosis or restenosis in a subject, including identifying a subject suspected of needing inhibition of atherosclerosis or restenosis and administering to the subject PTU in an amount sufficient to prevent atherosclerosis or restenosis in the subject. The present invention further discloses an article of manufacture including a medical device and PTU.

82 Claims, 20 Drawing Sheets

OTHER PUBLICATIONS

Konneh et al, Atherosclerosis 113:29–39 (1995), Vitamin E inhibits the intimal response to balloon catheter injury in the carotid artery of the cholesterol–fed rat.

Ross, N Engl J Med 340:115–126 (1999), Atherosclerosis—An Inflammatory Disease.

Serruys et al, N Engl J Med 331:489–495 (1994) A Comparison of Balloon–Expandable–Stent Implantation With Balloon Angioplasty In Patients With Coronary Artery Disease.

Post et al, Circulation 89:2816–2821 (1994) The Relative Importance Of Aterial Remodeling Compared With Intimal Hyperplasia In Lumen Renarrowing After Balloon Angioplasty.

Painter et al. 75:398–400 (1995), Serial Intravascular Ultrasound Studies Fail to Show Evidence of Chronic Palmaz–Schatz Stent Recoil.

Honda et al, Circulation 104:380–383 (2001), Inravascular Ultrasound Observations From the First Human Experience With the QP2–Eluting Polymer Stent System.

* cited by examiner

CHO

A. smooth muscle cells    B. macrophages

CHO+PTU

C. smooth muscle cells    D. macrophages

A

B

A  B

C                                    D (A) Collagen type I (B) Collagen type III (C) RNA gel C  0.38  0.5  0.76   C  0.38  0.5  0.76   C   0.38  0.5  0.76 (mM)

1 D             2 D             3 D (A) Collagen type I (B) Collagen type III (A) Negative control    (B) Control    (C) PTU (A) Negative control   (B) Control   (C) PTU

PREVENTION OF ATHEROSCLEROSIS AND RESTENOSIS

The present application claims benefit of priority to the following applications, which are incorporated by reference in its entirety herein: U.S. Provisional Patent Application No. 60/345,766, entitled "Propylthiouracil in Atherogenesis", filed on 4 Jan. 2002 and Republic of China (Taiwan) Provisional Patent Application No. 91113579 entitled "Propylthiouracil in Atherogenesis", filed on Jun. 21, 2002.

TECHNICAL FIELD

The present invention relates generally to the fields of vascular disease and cardiology, and more specifically concerns pharmaceutical compositions, methods of use thereof, and medical devices for preventing or treating atherosclerosis and restenosis or both.

BACKGROUND

Atherosclerosis, the most common form of vascular disease, is the disorder of large arteries that underlies most coronary artery disease, aortic aneurysm, and arterial disease of lower extremities, and is believed to play a major role in cerebrovascular disease (Libby, in "The Principles of Internal Medicine", 15th ed., Braunward et al. (editors), Saunders, Philadelphia, Pa., 2001, pp. 1377–1382.). One theory for pathogenesis of atherosclerosis that is consistent with a variety of experimental evidence is the "reaction to injury" hypothesis (Libby, in "The Principles of Internal Medicine", 15th ed., Braunward et al. (editors), Saunders, Philadelphia, Pa., 2001, pp. 1377–1382.). The injury to the endothelium may be subtle, resulting in a loss of the ability of the cells to function normally. Examples of types of injury to the endothelium include hypercholesterolemia and mechanical stress (Ross, 1999, N. Engl. J. Med., 340: 115). Dysfunction of endothelial cells is believed to trigger a sequence of events including monocyte and platelet adherence, migration of monocytes into intima where they become macrophages, and release of macrophage secretory products, including growth factors and cytokines, which, in conjunction with plasma constituents such as lipoproteins, form foam cells in the vascular wall (Ross, 1999, N. Engl. J. Med., 340: 115). This is believed to stimulate the proliferation of intimal smooth muscle cells at these sites of injury, where these proliferating smooth muscle cells deposit extracellular connective tissue matrix and accumulate lipid, forming an atherosclerotic plaque (Ross, 1999, N. Engl. J. Med., 340: 115).

Percutaneous transluminal coronary balloon angioplasty is a widely used technique for recanalizing arteries that are occluded by atherosclerotic plaque, but its usefulness is limited by the occurrence of restenosis in high proportion of patients (Serruys et al., 1988, Circulation, 77:361). Intracoronary stents have been shown to reduce the incidence of restenosis compared with balloon angioplasty in randomized trials of specific patient groups (Serruys et al., 1994, N. Engl. J. Med., 331:489). The reduction in restenosis achieved with these devices results from greater initial lumen gain, prevention of elastic recoil, and attenuation of the arterial remodeling process (Post et al., 1994, Circulation, 89:2816; Painter et al., 1995, Am. J. Cardiol., 75:398). However, the long-term clinical efficacy of intracoronary stenting is also limited by restenosis, which occurs in 15% to 30% of patients (Serruys et al., 1994, N. Engl. J. Med., 331:489).

In-stent restenosis is believed to be due to neointimal hyperplasia (Serruys et al., 1994, N. Engl. J. Med., 331:489). Stent-induced mechanical arterial injury and a foreign-body response to the prosthesis are believed to result in acute and chronic inflammation in the vessel wall, leading to production of cytokines and growth factors (Serruys et al., 1994, N. Engl. J. Med., 331:489). These are believed to activate multiple signaling pathways, inducing vascular smooth muscle cell (VSMC) proliferation, which is believed to result in neointimal hyperplasia (Serruys et al., 1994, N. Engl. J. Med., 331:489). In addition to VSMC proliferation, VSMC migration and phenotypic differentiation, as well as extracellular matrix formation and degradation are believed to determine the extent of neointimal formation (Newby and George, 1996, Curr. Opin. Cardiol., 11:547). The predominant feature of late restenosis lesions is a large amount of extracellular matrix with a reduced number of smooth muscle cells, whereas in the early stages of intimal thickening formation the number of smooth muscle cells is increased (Pauletto et al., 1994, Clin. Sci., 87:467). To successfully prevent neointimal formation and restenosis, compounds that exert multifactorial effects on cellular activation and extracellular matrix constituents are likely to be necessary, and restenosis prevention using an approach that targets only one causative factor is believed to lack promise (Rosanio et al., 1999, Thromb. Haemost., 82(S1):164).

Drug-eluting or drug-coated stents are a more recent approach to preventing restenosis. Two anti-cancer drugs, sirolimus and paclitaxel, have been used to coat stents, which elute these hyperplasia-inhibiting drugs following implantation (Sousa et al., American Heart Association Scientific Sessions, Nov. 11–14, 2001, Anaheim, Calif., Abstract 115154; Grube et al., American Heart Association Scientific Sessions, Nov. 11–14, 2001, Anaheim, Calif., Abstract 110945). The first human clinical trial with sirolimus-coated stents (the RAVEL trial) followed patients for more than 6 months, with 0 out of 188 patients showing restenosis, and 0 out of 188 patients exhibiting early or late stent thrombosis (Sousa et al., American Heart Association Scientific Sessions, Nov. 11–14, 2001, Anaheim, Calif., Abstract 115154). The efficacy of the paclitaxel-coated stent also appears promising (Honda et al., 2001, Circulation, 104:380). Based on these early results, drug-eluting stents are believed to promise major impact on the treatment of coronary artery disease in the near future.

Both sirolimus and paclitaxel were initially developed as anticancer agents because of their cytostatic ability to inhibit cellular proliferation and migration (Poon et al., 1996, J. Clin. Invest., 98:2277; Rowinsky and Donehower, 1995, N. Engl. J. Med., 332:1004). However, these cytostatic effects are not specific for vascular smooth muscle cells. They were also found to inhibit the proliferation of vascular endothelial cells (Verin at al, 2001, Am. J. Physiol., 281:L565), which may delay endothelialization after stenting resulting in late thrombosis in clinical usage (Liistro and Colombo, 2001, Heart, 86:262).

SUMMARY

Figure 1A:
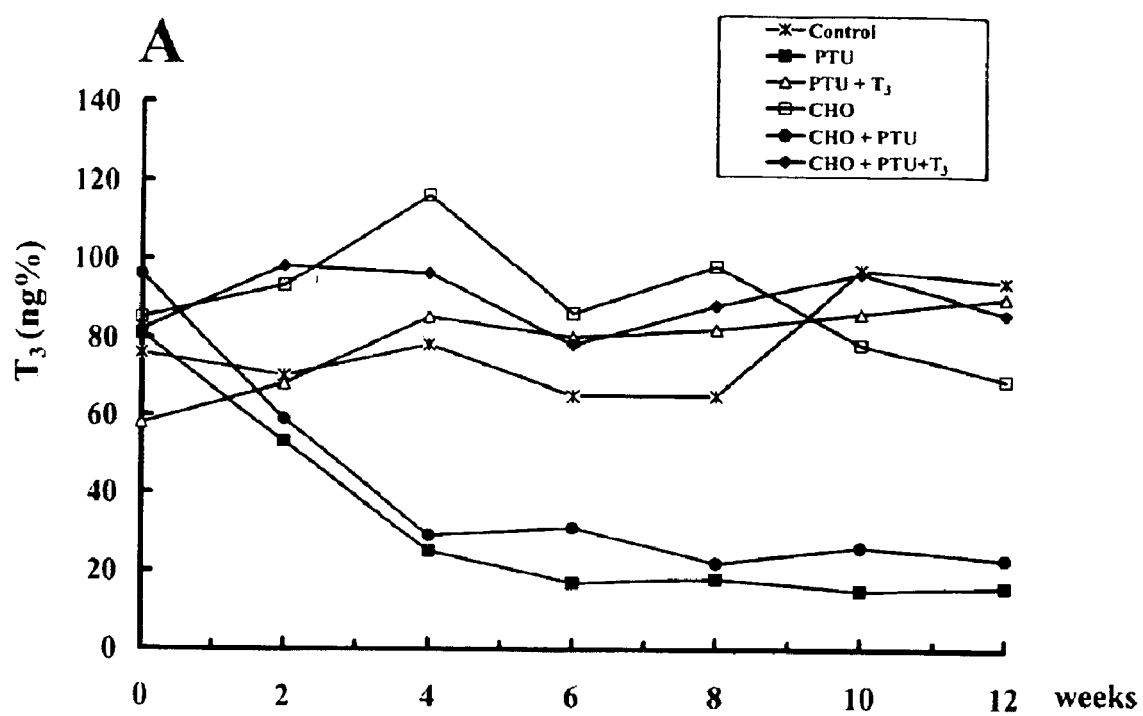
FIG. 1 depicts time-related changes in serum triiodothyronine ($T_3$) (FIG. 1A) and serum total cholesterol (CHO) levels (FIG. 1B) during the study period. The six treatment groups were rabbits assigned randomly to either a normal chow diet and receiving either no drug (Control), propylthiouracil (PTU), or propylthiouracil and triiodothyronine hormone (PTU+$T_3$), or to a 2% cholesterol diet (Cat. #57317-9, Purina Mills Inc, USA) and receiving either no drug (CHO), propylthiouracil (CHO+PTU), or propylthiouracil and triiodothyronine hormone (CHO+PTU+$T_3$) as shown in Table 2. Points plotted are mean values. Serum triiodothyronine ($T_3$) decreased to unmeasurable levels after 4 weeks of treatment with propylthiouracil (PTU). This hypothyroid effect could be reversed by a concomitant supplement with triiodothyronine (CHO+PTU+$T_3$) (FIG. 1A). Serum cholesterol levels rose rapidly after high-cholesterol feeding (FIG. 1B). However, compared with the control group, rabbits that consumed propylthiouracil (PTU) and not triiodothyronine ($T_3$) showed a slight increase in serum cholesterol levels.
Figure 1B:
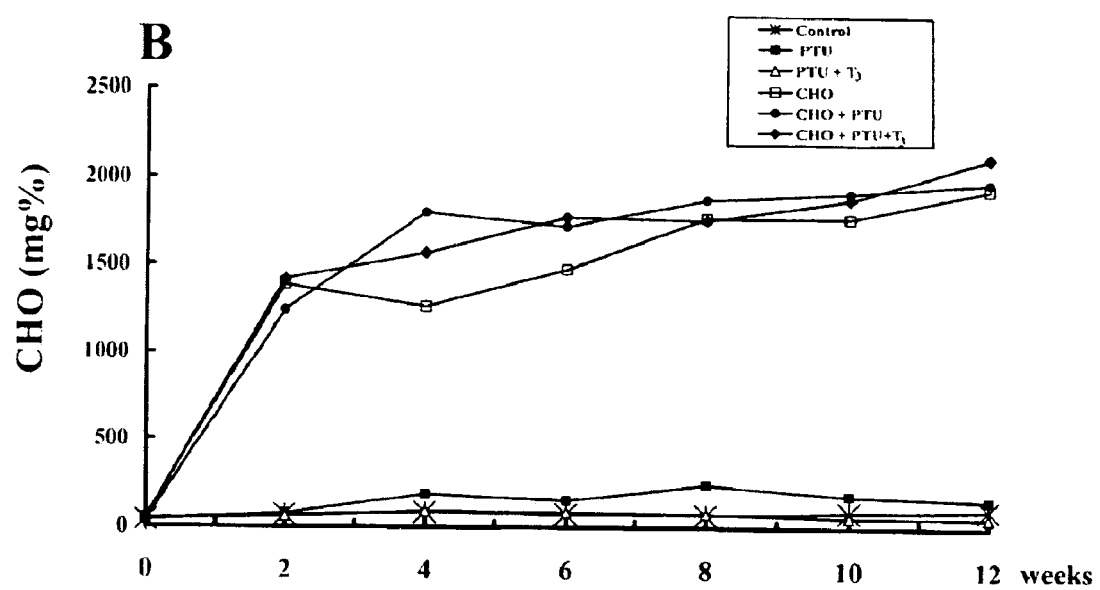

The present invention recognizes the need for effective treatment for treating or preventing atherosclerosis and restenosis and provides compositions, methods of use thereof, and medical devices with related benefits.

A first aspect of the present invention is a pharmaceutical composition including a pharmaceutically acceptable carrier, and propylthiouracil in an amount sufficient to prevent or treat atherosclerosis or restenosis in a subject. The pharmaceutical composition can be in any appropriate form, such as but not limited to a solution, a suspension, and aqueous suspension, a capsule, a powder, a syrup, an emulsion, liposomes, a suppository, or a complex. The pharmaceutical composition can also include an appropriate pharmaceutically acceptable preservative, dye or flavoring. The pharmaceutically acceptable carrier can be any that is appropriate, such as but not limited to water, physiological saline, an alcohol, dimethylsulfoxide, a physiologically compatible buffer, or a pharmaceutically acceptable excipient.

Propylthiouracil is provided in an amount sufficient to prevent atherosclerosis. Propylthiouracil can be provided to achieve serum levels between about three micrograms per milliliter and about seven (7) micrograms per milliliter or between about one (1) microgram per milliliter and about ten (10) micrograms per milliliter in the subject to achieve this effect, but other concentrations could be used and the effect confirmed. The propylthiouracil can be administer to the subject at a does of between about 1 milligram per kilogram per day and about ten (10) milligrams per kilogram per day or between about 0.1 milligram per kilogram per day to about 20 milligrams per kilogram per day to achieve this effect, but other concentrations could be used and the effect confirmed.

In one aspect of the present invention a subject is suspected of having, has been diagnosed as having, or is at risk of developing atherosclerosis, coronary artery disease, or stroke. In another aspect of the present invention the subject is suspected of having, has been diagnosed as having, or is at risk of developing restenosis. In yet another aspect of the present invention the subject is to undergo vascular surgery, angioplasty, balloon angioplasty, insertion of a prosthesis, insertion of a graft, insertion of a stent, catheterization, or arterial blockage evaluation. Preferably the subject is a human.

Administration of the pharmaceutical composition can include a variety of routes of administration, such as but not limited to oral, intravenous, parenteral, intramuscular, subcutaneous, rectal, intraventricular, intraatrial, intraaortal, intraarterial, or intraperitoneal administration. Administration can be by a medical device such as but not limited a catheter, a balloon, an implantable device, a prosthesis, a graft, or a stent, wherein such medical device contains Propylthiouracil that can be released over time to have the desired effect.

Propylthiouracil can be provided in an amount sufficient to inhibit vascular smooth muscle cell proliferation in the subject. Preferably propylthiouracil is provided in an amount sufficient to inhibit vascular smooth muscle cell proliferation but not substantially inhibit endothelial cell proliferation in the subject. Preferably propylthiouracil is provided in an amount sufficient to inhibit vascular smooth muscle cell proliferation but not substantially cause vascular smooth muscle cell cytotoxicity or vascular smooth muscle cell apoptosis in the subject. Preferably propylthiouracil is provided in an amount sufficient to decrease collagen expression in vascular tissue in the subject. Preferably propylthiouracil is provided in an amount sufficient to promote conversion of vascular smooth muscle cells from a non-contractile phenotype to a contractile phenotype in the subject. Preferably propylthiouracil is provided in an amount sufficient to inhibit migration activity of vascular smooth muscle cells in the subject.

In a second aspect of the present invention a method of inhibiting or treating atherosclerosis or restenosis in a subject is disclosed including identifying a subject suspected of needing inhibition of atherosclerosis or restenosis, and administering to the subject propylthiouracil in an amount sufficient to prevent atherosclerosis or restenosis in the subject. The subject may be identified by methods such as evaluation of the subject's health history, conducting a physical examination, or by performing clinical testing.

In a third aspect of the present invention an article of manufacture is disclosed including a medical device, and propylthiouracil. The medical device can be an implantable device, catheter, a balloon, or a stent. The medical device can be a biodegradable device, a prosthetic device, a stent, a graft, a shunt, a suture, a patch, a prosthetic valve, or a prosthetic heart.

Propylthiouracil can be provided on or within the medical device as a coating, membrane, film, impregnated matrix, a polymer, a sponge, a gel, or a porous layer. Propylthiouracil may be released from the medical device over a substantial period of time or over a short period of time when provided within the subject. The dose can be those previously described or at localized serum levels between about one hundred (100) micrograms per milliliter and about one thousand (1,000) micrograms per milliliter. Propylthiouracil can be provided in or on such medical devices using methods known in the art, such as, for example, coatings or impregnations.

The medical devices of the present invention can be used alone or in combination. For example, for balloon angioplasty followed by insertion of stent, one or both of the balloon device and stent device can include Propylthiouracil at the appropriate concentration and release characteristics to produce the desired effect.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate the plural of that term. Likewise, were a terms is provided in the plural, the inventors also contemplate the singular of that term. The nomenclature used herein and the laboratory procedures described below are those well known and commonly employed in the art. Were there are discrepancies in terms and definitions used in references that are incorporated by reference herein, the terms used in this application shall have the definitions given herein.

I. Pharmaceutical Composition

The present invention provides a pharmaceutical composition including a pharmaceutically acceptable carrier and propylthiouracil in an amount sufficient to prevent atherosclerosis or restenosis in a subject.

Propylthiouracil

Propylthiouracil has the chemical formula $C_7H_{10}ON_2S$ and a molecular weight of about 170.23 grams per mole. Propylthiouracil is synonymous with 6-n-propyl-2-thiouracil, 4-hydroxy-2-mercapto-6-n-propylpyrimidine, and 2,3-dihydro-6-n-propyl-2-thioxo-4(1H)-pyrimidinone. Propylthiouracil has been assigned the CAS registry number 51-52-5.

Propylthiouracil ("PTU") is used in the treatment of hyperthyroidism patients because of its hypothyroid effect. Propylthiouracil is believed to inhibit the oxidation of iodide, iodination of monoiodotyrosine, and coupling steps in thyroxine production as well as the peripheral conversion of thyroxine ($T_4$) to triiodothyronine ($T_3$) (Mechanick and Davies, in "Thyroid Disease", 2nd ed., Falk (ed.), Lippincott-Raven Publishers, Philadelphia, Pa., 1997, pp. 253–296). Propylthiouracil was demonstrated to reduce alcohol-induced hepatocyte damage and severe alcoholic liver disease, although the mechanism for this protective effect is unknown (Orrego et al., 1987, *N. Engl J. Med.*, 17:1421). It is believed that propylthiouracil may act as an antioxidant (Hicks et al., 1992, *Biochem. Pharmacol.*, 43:439; Ross et al., 1998, *J. Pharmacol. Exp. Therapeutics*, 285:1233). Several antioxidants, such as probucol (Ferns et al., 1992, *Proc. Natl. Acad. Sci.*, 89:11312), butylated hydroxytoluene (Freyschuss et al., 1993, *J. Clin. Invest.*, 91:1282), and vitamin E (Konneh et al., 1995, *Atherosclerosis*, 113:29), have been shown to prevent the progression of atherosclerosis.

For the purposes of the present invention, the term "propylthiouracil" or "PTU" also encompasses oxidized dimeric propylthiouracil (that is to say, the symmetrical disulfide), propylthiouracil tautomers, propylthiouracil complexes, and propylthiouracil salts. Propylthioruacil tautomers include for example the enol and keto forms of the conjugated ketone functionality of the pyrimidine ring, and the thioxo and thiol forms of the thiol/thioxo moiety. Propylthiouracil complexes include but are not limited to propylthiouracil or propylthiouracil salts complexed with a complexing agent such as a crown ether or a cyclodextrin (Chiesi et al., U.S. Pat. No. 5,773,029). Propylthiouracil salts include but are not limited to, alkali metal or quaternary ammonium salts of propylthiouracil.

Pharmaceuticaly Acceptable Carrier

Pharmaceutical compositions of the present invention can include, in addition to propylthiouracil in an amount sufficient to prevent atherosclerosis or restenosis in a subject, a pharmaceutically acceptable carrier. Suitable pharmaceutically acceptable carriers include diluents, excipients, or carrier materials, selected according to the intended form of administration and consistent with conventional pharmaceutical practice. Examples of suitable carriers include but are not limited to water, physiological saline, phosphate-buffered saline, a physiologically compatible buffer, saline buffered with a physiologically compatible salt, a water-in-oil emulsion, and an oil-in-water emulsion, an alcohol, dimethylsulfoxide, dextrose, mannitol, lactose, glycerin, propylene glycol, polyethylene glycol, polyvinylpyrrolidone, lecithin, albumin, sodium glutamate, cysteine hydrochloride, and the like, and mixtures thereof.

The pharmaceutically acceptable carrier can also include appropriate pharmaceutically acceptable antioxidants or reducing agents, preservatives, suspending agents, solubilizers, stabilizers, chelating agents, complexing agents, viscomodulators, disintegrating agents, binders, flavoring agents, coloring agents, odorants, opacifiers, wetting agents, pH buffering agents, and mixtures thereof, as is consistent with conventional pharmaceutical practice ("Remington: The Science and Practice of Pharmacy", 20th edition, Gennaro (ed.) and Gennaro, Lippincott, Williams & Wilkins, 2000).

Pharmaceutical compositions of the present invention can be formulated and provided in any formulation suitable to the intended form of administration and consistent with conventional pharmaceutical practice ("Remington: The Science and Practice of Pharmacy", $20^{th}$ edition, Gennaro (ed.) and Gennaro, Lippincott, Williams & Wilkins, 2000). Examples of suitable formulations include tablets, capsules, syrups, elixirs, ointments, creams, lotions, sprays, aerosols, inhalants, solids, powders, particulates, gels, suppositories, concentrates, emulsions, liposomes, microspheres, dissolvable matrices, sterile solutions, suspensions, or injectables, and the like. Injectables can be prepared in conventional forms either as liquid solutions or suspensions, as concentrates or solid forms suitable for solution or suspension in liquid prior to injection, or as emulsions.

Amount Sufficient to Prevent Atherosclerosis or Restenosis

Pharmaceutical compositions of the present invention contain propylthiouracil in an amount sufficient to prevent or treat atherosclerosis or restenosis in a subject. The actual amount of propylthiouracil will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, route of administration, regime, and purity and activity of the composition. This amount can be an amount sufficient to achieve serum propylthiouracil levels of between about 1 microgram per milliliter and about 10 micrograms per milliliter in the subject, or an amount sufficient to achieve serum propylthiouracil levels of between about 3 micrograms per milliliter and about 7 micrograms per milliliter in the subject. Expressed as a daily dose, this amount can be between about 0.1 milligrams per kilogram body weight per day and about 20 milligrams per kilogram body weight per day, or between about 1 milligram per kilogram body weight per day and about 10 milligrams per kilogram body weight per day.

Subject

Pharmaceutical compositions of the present invention are suitable for administration to a subject in need of prophylaxis or therapy of cardiovascular diseases and related conditions. The subject is preferably a human but can be non-human as well. A suitable subject can be an individual who is suspected of having, has been diagnosed as having, or is at risk of developing atherosclerosis, coronary artery disease, stroke, restenosis, vascular fibromuscular dysplasia, polyarteritis nodosa, Takayasu's arteritis, and like conditions as can be determined by one knowledgeable in the art. Another example of a suitable subject is an individual who is to undergo vascular surgery, including but not limited to vascular bypass surgery, atherectomy, endatherectomy, laser ablation, angioplasty, balloon angioplasty, cardiac allograft (cardiac transplant), insertion of a prosthesis, insertion of a graft, insertion of a stent, catheterization, or arterial blockage evaluation.

Route of Administration

Depending on the specific conditions being treated, pharmaceutical compositions of the present invention can be formulated and administered systemically or locally. Techniques for formulation and administration can be found in "Remington: The Science and Practice of Pharmacy" ($20^{th}$ edition, Gennaro (ed.) and Gennaro, Lippincott, Williams & Wilkins, 2000). Suitable routes of administration can include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The pharmaceutical compositions of the present invention can be administered to the subject by a medical device, such as, but not limited to, catheters, balloons, implantable devices, biodegradable implants, prostheses, grafts, sutures, patches, shunts, or stents.

Activity and Endpoints

Pharmaceutical compositions of the present invention can contain propylthiouracil in an amount sufficient to inhibit vascular smooth muscle cell proliferation in the subject. Preferably, this amount is sufficient to inhibit vascular smooth muscle cell proliferation but not substantially inhibit endothelial cell proliferation in the subject. Also preferably, this amount is sufficient to inhibit vascular smooth muscle cell proliferation but not substantially cause vascular smooth muscle cell cytotoxicity or vascular smooth muscle cell apoptosis in the subject.

Pharmaceutical compositions of the present invention can contain propylthiouracil in an amount sufficient to decrease collagen expression in vascular tissue in the subject. The pharmaceutical compositions can contain propylthiouracil in an amount sufficient to promote conversion of vascular smooth muscle cells from a non-contractile phenotype to a contractile phenotype in the subject. The pharmaceutical compositions can contain propylthiouracil in an amount sufficient to inhibit migration activity of vascular smooth muscle cells in the subject.

Figure 6A:
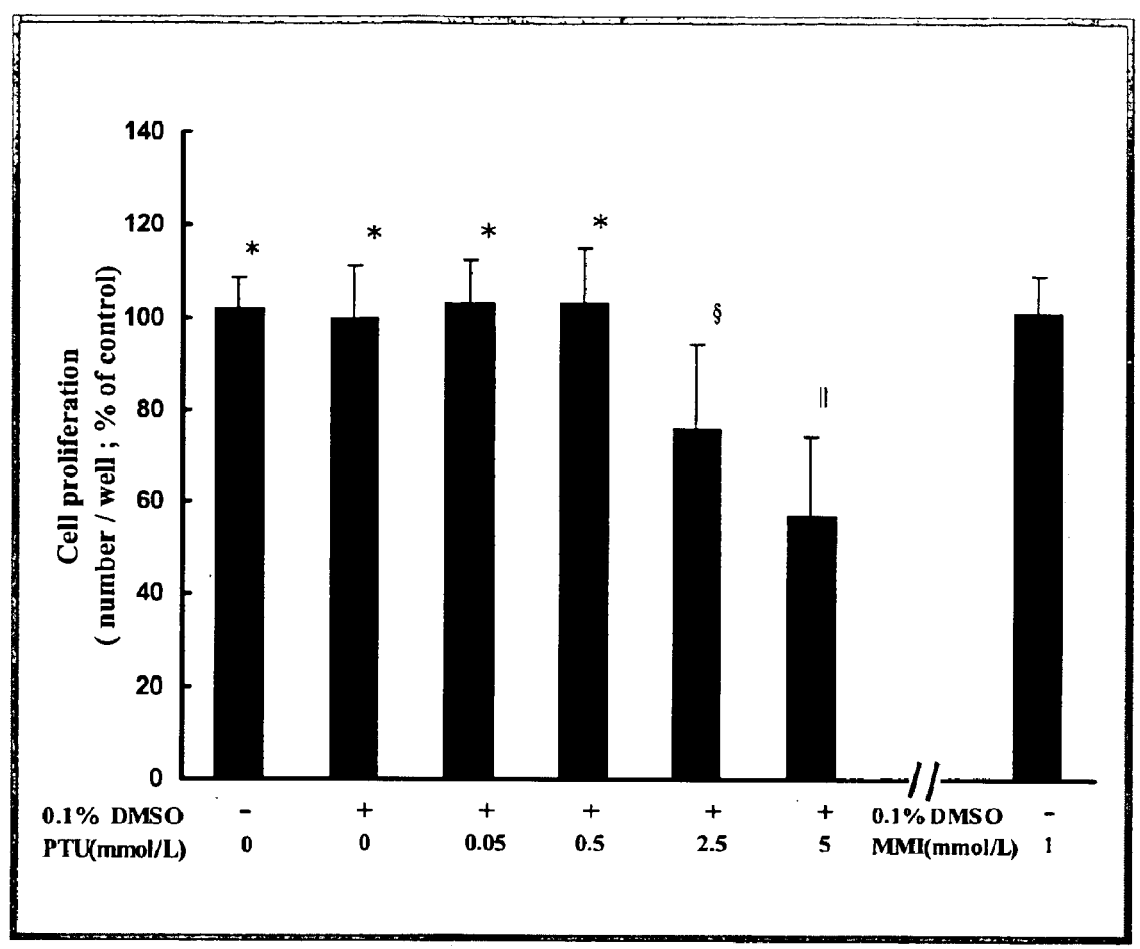
FIG. 6 depicts the effects of propylthiouracil (PTU) and methimazole (MMI) on cell proliferation (FIG. 6A) and on DNA synthesis (FIG. 6B) in rat vascular smooth muscle cells (from rat thoracic aorta prepared according to Example 2), expressed as a percentage of the number of cells per well (FIG. 6A) and thymidine incorporation rate as counts per minute per 100 milligrams protein (FIG. 6B) of control cells maintained in medium containing 0.1% dimethylsulfoxide as vehicle. Each value is a mean±SD ($n=6$). $P<0.001$; *, §, ∥: different symbols represent significant difference between groups using Tukey's multiple comparison. Propylthiouracil (PTU), but not methimazole (MMI), significantly inhibited the growth of VSMCs and thymidine incorporation into VSMCs in a concentration-dependent manner.
Figure 6B:
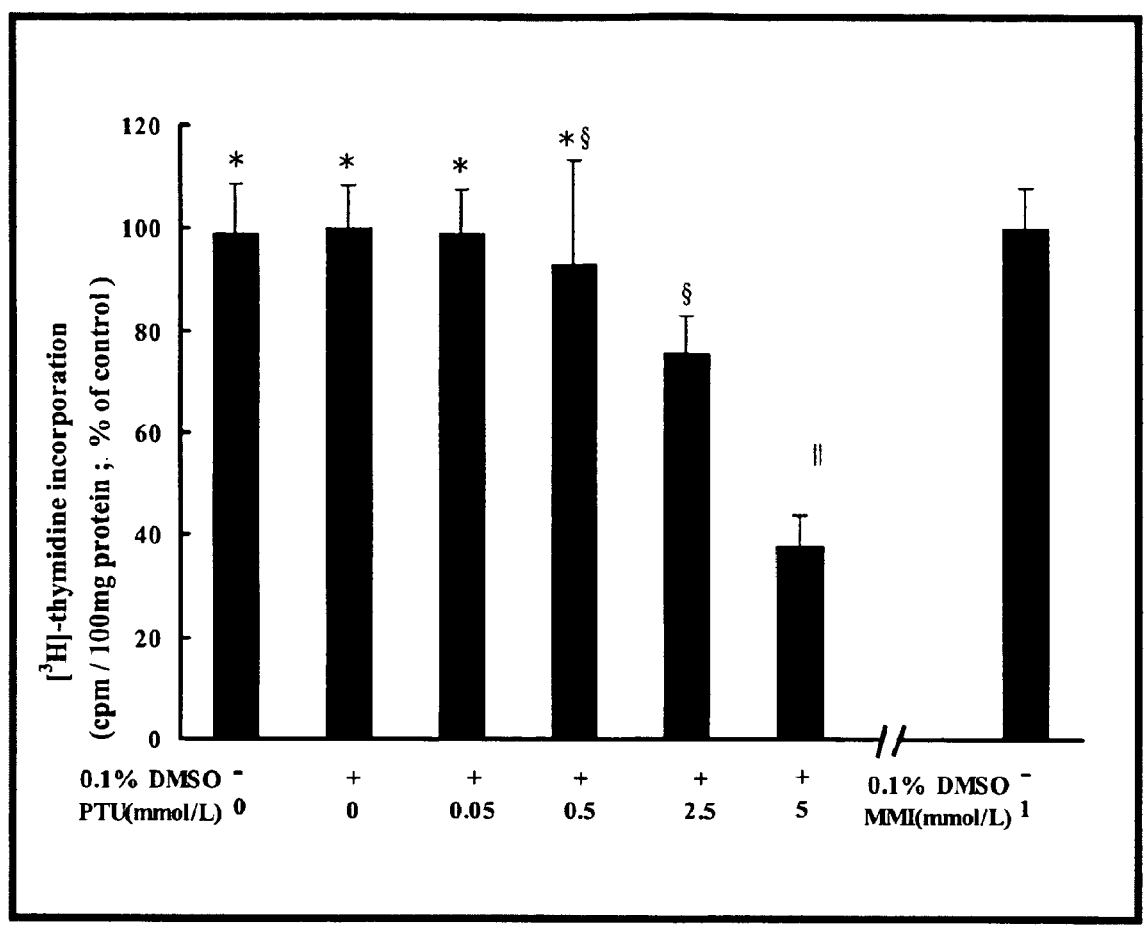
Figure 7:
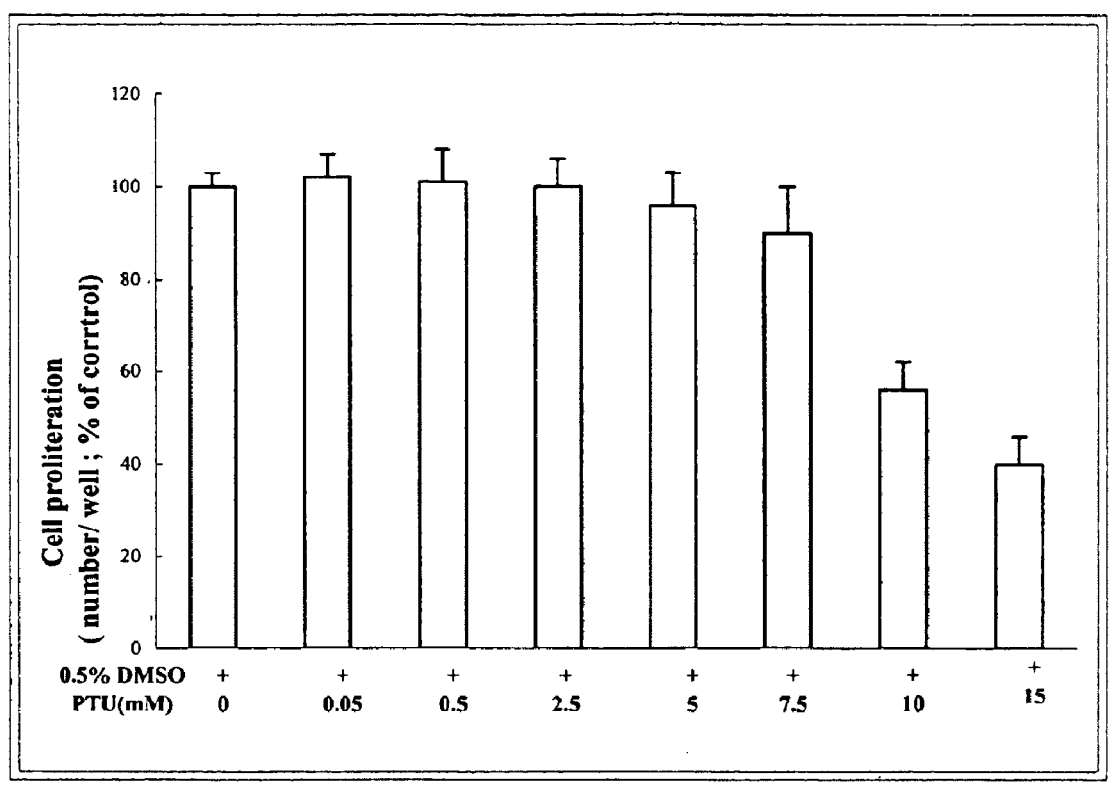
FIG. 7 depicts the effects of propylthiouracil (PTU) on cell proliferation in human vascular endothelial cells (from human umbilical vein prepared according to Example 2), expressed as a percentage of the number of control cells maintained in medium containing 0.1% dimethylsulfoxide (DMSO) as vehicle. The inhibitory effect of propylthiouracil (PTU) on vascular endothelial cells was less potent than on vascular smooth muscle cells (a difference of 20–30%).
Figure 9:
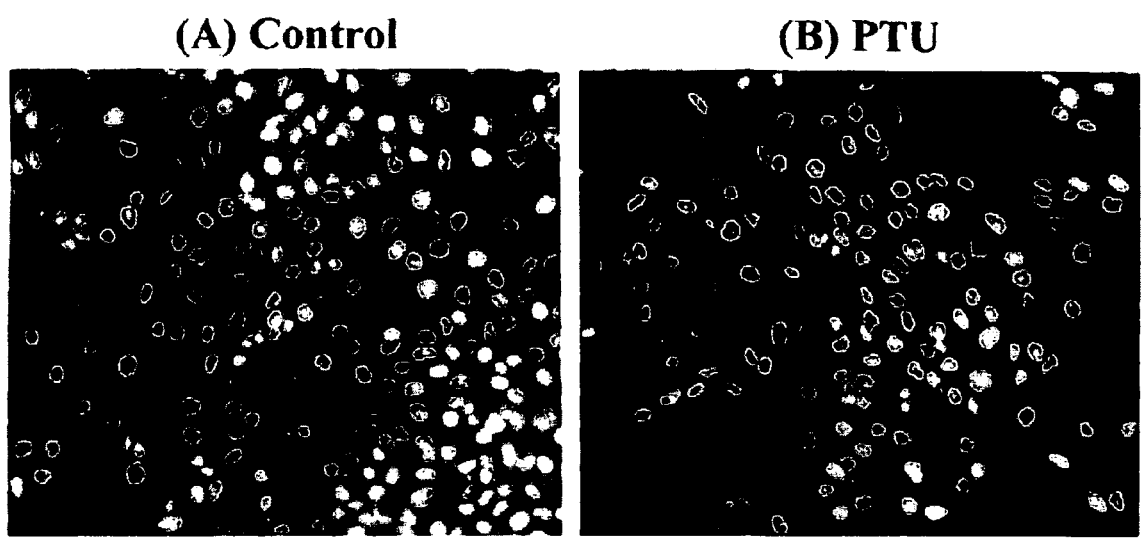
FIG. 9 depicts effects of propylthiouracil (PTU) on PI-stained DNA in rat vascular smooth muscle cells. After 24 hours of incubation, rat vascular smooth muscle cells were treated without (FIG. 9A) or with 5 millimolar propylthiouracil (PTU) (FIG. 9B) for 24 hours. Rat vascular smooth muscle cells were fixed with 4% paraformaldehyde, and morphological changes were examined under fluorescent microscope (magnification of objective lens, ×200) after DNA stained with propidium iodide. Propylthiouracil (PTU) even at the highest concentration (5 millimolar) did not cause any pyknosis or karyorhexis (typical changes of apoptosis) in VSMCs (FIG. 9B) compared with control VSMCs (FIG. 9A).
Figure 10:
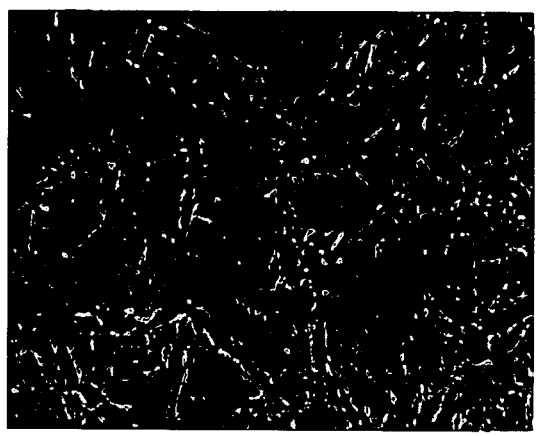
FIG. 10 depicts the effects of propylthiouracil (PTU) on the morphology of vascular smooth muscle cells. Rat vascular smooth cells isolated according to Example 2 were treated with 5 millimolar propylthiouracil added to the medium (PTU, Panel B) underwent a change to a highly elongated and spindle-shaped morphology, compared to the control cells (Panel A). These morphological changes were evident after 12 hours and complete by 72 hours.
Figure 10:
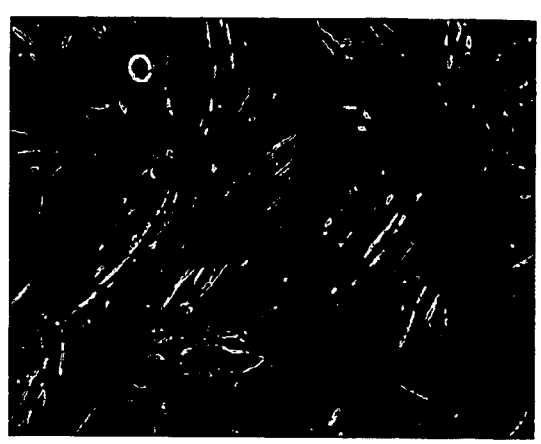
Figure 11A:
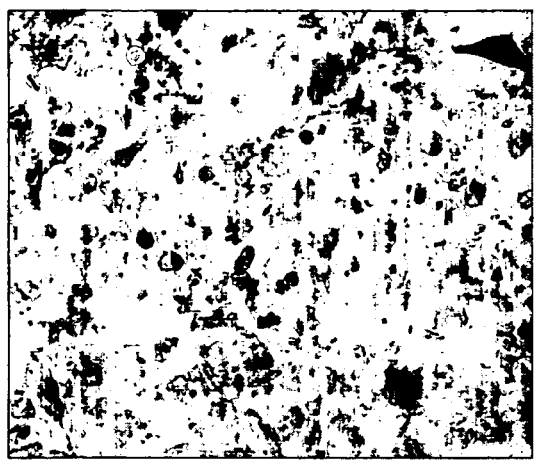
FIG. 11 depicts the effects of propylthiouracil (PTU) on the phenotypic change of rat vascular smooth muscle cells isolated according to Example 2. Immunocytochemical staining for expression of proteins specific for contraction in vascular smooth muscle cells treated with 5 millimolar propylthiouracil for 24 hours (FIGS. 11A and 11B, Panels B and D) according to Example 4 demonstrated an increase in both alpha-actin (FIG. 11A) and calponin (FIG. 11B), compared to the control cells (Panels A and C). Therefore, vascular smooth muscle cells, when cultured on propylthiouracil (PTU)-containing medium, show a contractile phenotype, as indicated by a spindle-like shape and a high level expression of contractile proteins.
Figure 11A:
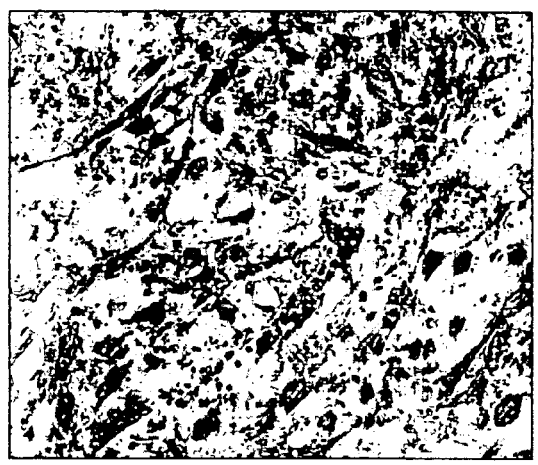
Figure 11B:
Figure 11B:
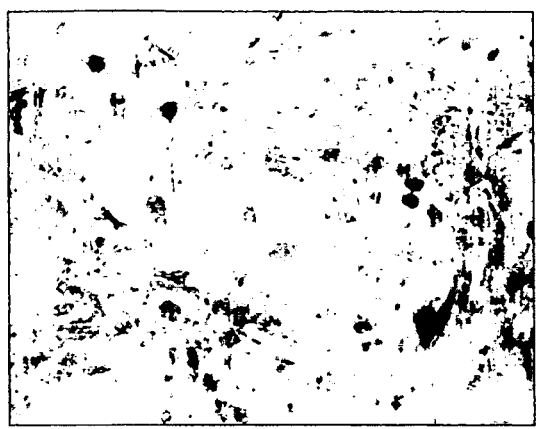
Figure 16:
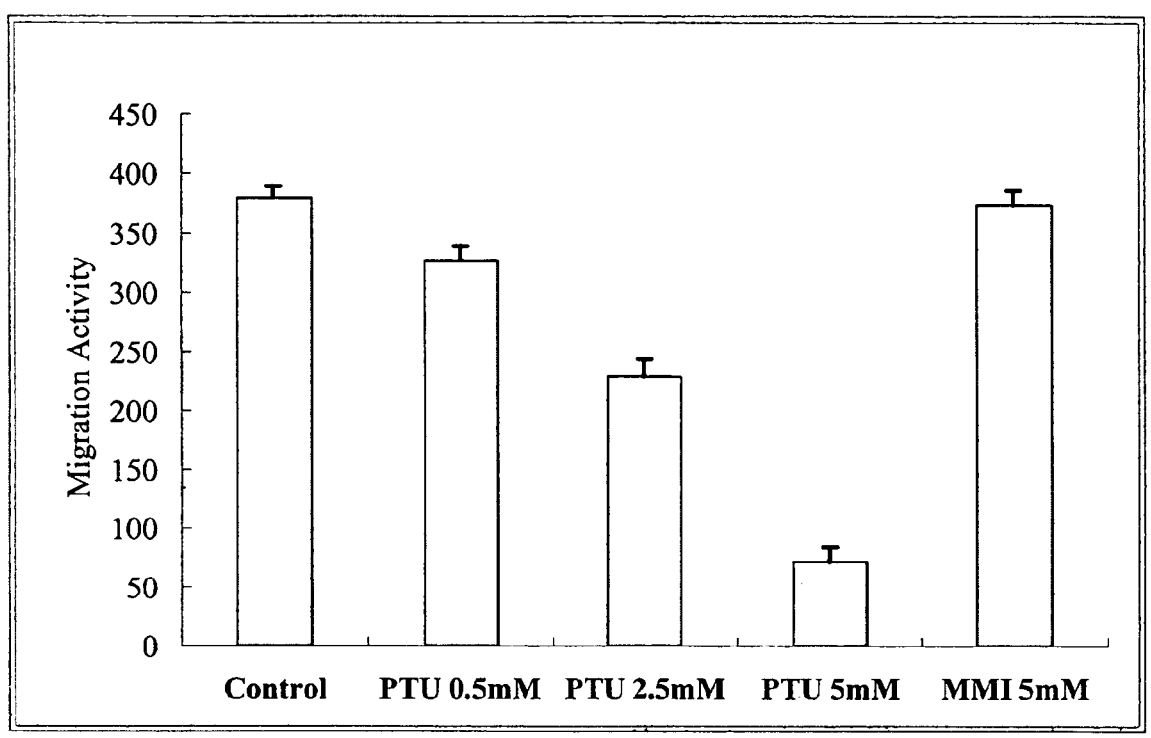
FIG. 16 depicts the effects of propylthiouracil (PTU) and methimazole (MMI) on the migration activity of vascular smooth muscle cells. Rat vascular smooth muscle cells ($1\times10^6$ cells) were added to the apical chamber of transwell culture dishes, incubated for 5 hours, cells that migrated from the apical chamber, through the dividing filter, and into the basal chamber were fixed, stained with Giemsa solution, and counted under the light microscope. Migration activity was expressed as the number of cells in the basal chamber. Each value is a mean±SD (n=5). propylthiouracil (PTU) treatment demonstrated inhibition of the migration of vascular smooth muscle cells in a concentration-dependent manner.

The activity of propylthiouracil's anti-atherosclerotic effect was further investigated with a number of in vitro studies using cultured rabbit and rat vascular smooth muscle cells (VSMCs). In one study, exogenous administration of propylthiouracil, but not methimazole (another anti-thyroid drug), in the cell culture medium led to a concentration-dependent inhibition of rat VSMC proliferation (FIG. 6A) and [$^3$H]thymidine incorporation into the VSMC nuclei (FIG. 6B). However, the inhibitory effect of propylthiouracil on human endothelial cell proliferation was less potent ($IC_{50}$ at 5.8 millimolar for VSMCs and $IC_{50}$ at 12 millimolar for endothelial cells)(FIG. 7). Furthermore, the lack of evidence for apoptosis occurring in propylthiouracil-treated rat VSMCs suggests that the antiproliferative effect of PTU on rat VSMCs may not be mediated by an apoptotic process (FIG. 9). Propylthiouracil converted rat VSMCs from a noncontractile phenotype to a contractile (quiescent) phenotype (FIG. 10 and FIG. 11). Propylthiouracil decreased rat VSMC expression of pro-alpha-1(I) collagen gene, a major extracellular matrix protein in the arteries (FIGS. 12,13,14, and 15). Finally, propylthiouracil inhibited rat VSMC migration (FIG. 16).

Results show that the anti-atherosclerotic effect of propylthiouracil is not thyroid-mediated and involves multifactorial effects, including inhibition of VSMC proliferation and migration, inhibition of collagen expression in VSMCs, and conversion of VSMCs to a contractile phenotype. These results suggest propylthiouracil can be a potentially effective drug in preventing or treating restenosis or atherosclerosis.

Depending on the dosage used, the systemic administration of propylthiouracil for the prevention of atherosclerosis or restenosis may produce effects such as hypothyroidism (Mechanick and Davies, in "Thyroid Disease", 2nd ed., Falk (ed.), Lippincott-Raven Publishers, Philadelphia, Pa., 1997, pp. 253–296). Localized delivery, for example by using a stent platform, a drug-delivery catheter, a biodegradable implant, or other suitable methods, can permit deposition of a therapeutically or prophylactically effective amount of propylthiouracil in the particular tissues where prevention or treatment of atherosclerosis or restenosis is desired. In contrast to sirolimus and paclitaxel, propylthiouracil inhibited the proliferation of smooth muscle cells but not of vascular endothelial cells, which can have a beneficial effect for re-endothelialization after stenting. Propylthiouracil is therefore superior to sirolimus and paclitaxel as a stent drug for reducing neointimal hyperplasia. The anti-atherosclerotic activity of propylthiouracil is independent of its hypothyroid effects, and can thus be independent of propylthiouracil's thiocarbamide structure, which is believed to be responsible for propylthiouracil's hypothyroid effects. This suggests that it can be possible to modify the structure of propylthiouracil to preserve the anti-atherosclerotic activity while minimizing the hypothyroid effects.

Table 1 summarizes the effects of propylthiouracil and other compounds that have used in drug-eluting stents in mode of action, animal model, and human clinical studies of restenosis. Propylthiouracil inhibited the proliferation of smooth muscle cells but not vascular endothelial cells, which may prevent the occurrence of late thrombosis after stenting. Propylthiouracil converted vascular smooth muscle cells to a contractile (quiescent) status, which can preserve the contractile function of smooth muscle cells. Propylthiouracil, but not sirolimus or paclitaxel, reduced the synthesis of extracellular matrix, a major component of neointima formed in the vessel wall during restenosis, contributing to propylthiouracil's effectiveness in preventing the development of neointimal hyperplasia. Propylthiouracil has less systemic toxicity than sirolimus and paclitaxel, which have the potentially lethal side effects such as leukopenia and thrombocytopenia.

TABLE 1

Summary of Effects of Propylthiouracil and Other Compounds In Restenosis

| | Endothelial cellular function | SMC proliferation | SMC migration | Collagen expression | Phenotype change[A] | Anti-coagulation | Anti-inflammation | Effect on animal models of restenosis | | |
|---|---|---|---|---|---|---|---|---|---|---|
| | | | | | | | | Rat | Pig | Human |
| Sirolimus (Rapamycin) | + | ↓ | ↓ | ? | ? | − | + | + | + | + |
| Paclitaxel (Taxol) | − | ↓ | ↓ | ? | ? | − | + | + | + | + |
| All-trans retinoic acid | + | ↓ | ↓ | ↑ | + | − | − | + | ? | ? |
| Heparin | − | ↓ | ↓ | ↓ | − | + | − | + | + | − |
| Dexamethasone | ↓ | ↓ | ? | ↓ | ? | + | + | + | − | − |
| Estradiol | + | ↓ | ↓ | ↓ | ? | | + | + | + | − |
| Propylthiouracil | + | ↓ | ↓ | ↓ | + | ? | + | + | ? | ? |

[A]"+" represents the ability and a "−" represents the inability of conversion from a non-contracile phenotype to a contractile phenotype in an in vitro condition. A "↓" represents decrease and a "?" represents no data is available.

II. Method of Inhibiting Atherosclerosis or Restenosis

The present invention also provides a method of inhibiting atherosclerosisor restenosis in a subject including the steps of identifying a subject suspected of needing inhibition of atherosclerosis or restenosis and administering to the subject propylthiouracil (PTU) in an amount sufficient to prevent arteriosclerosis or restenosis in the subject.

Identifying a Subject Suspected of Needing Inhibition of Atherosclerosis or Restenosis The present invention's method of inhibiting arteriosclerosis or restenosis in a subject includes the process of identifying such a subject suspected of needing inhibition of atherosclerosis or restenosis can include evaluation of the subject's health history, conducting a physical examination, or by performing clinical testing. Preferably, this subject is a human. Evaluation of the subject's health history can include, for example, evaluation of pertinent risk factors such as hyperlipidemia, hypertension, cigarette or other tobacco habituation, diabetes mellitus, age, sex, diet and exercise habits, and family history. Physical examination can include, for example, evaluation of physical symptoms, such as blood pressure, electrocardiograms, exercise stress testing, pain symptoms, and imaging studies, such as ultrasonograms. Clinical testing can include evaluation of the subject's serum lipid profile and blood glucose and C-reactive protein levels. These methods of identifying a subject in need of inhibition of atherosclerosis or restenosis are well known in the art. Such a subject can be suspected of having, has been diagnosed as having, or is at risk of developing atherosclerosis s, coronary artery disease, stroke, or restenosis. Such a subject can also be an individual who is to undergo vascular surgery, including but not limited to vascular bypass surgery, atherectomy, endatherectomy, laser ablation, angioplasty, balloon angioplasty, cardiac allograft (cardiac transplant), insertion of a prosthesis, insertion of a graft, insertion of a stent, catheterization, or arterial blockage evaluation.

The subject identified as being in need of inhibition of atherosclerosis or restenosis as described herein is administered propylthiouracil in an amount sufficient to prevent atherosclerosis or restenosis in the subject. One skilled in the art can determine the appropriate dosage amount based on the particular formulation, route of administration, and dosage of the propylthiouracil-containing pharmaceutical composition, the specific nature of the condition to be treated, the individual subject, and other factors commonly considered. The exact formulation, route of administration, regime, and dosage can be chosen by the physician in view of the individual patient's condition ("Goodman & Gilman's The Pharmacological Basis of Therapeutics", $10^{th}$ edition, Hardman (ed.) and Limberd, McGraw-Hill Professional Publishing, New York, N.Y., 2001). It should be noted that the attending physician would know how to and when to terminate, interrupt, or adjust administration due to toxicity, organ dysfunction, or other adverse effects. Conversely, the attending physician would also know to adjust treatment to higher levels if the clinical response were not adequate. The magnitude of an administrated dose in the management of the disorder of interest will vary with the severity of the condition to be treated and to the route of administration. The severity of the condition can, for example, be evaluated in part by standard prognostic evaluation methods for that condition. Furthermore, the dose, and perhaps the dose frequency, will also vary according to the age, body weight, and response of the individual subject.

The amount of propylthiouracil administered to the subject in need of inhibition of atherosclerosis or restenosis as described herein can be an amount sufficient to achieve an appropriate serum levels or localized concentration. Such serum levels or localized concentrations are preferably between about 1 microgram per milliliter and about 10 micrograms per milliliter, or between about 3 microgram per milliliter and about 7 micrograms per milliliter, in the subject, although other levels or concentrations may be appropriate. The appropriate levels or concentrations for a particular subject, situation or medical device or procedure can be confirmed using appropriate animal models, appropriate extrapolations and appropriate clinical trials as is known in pharmacology. This dose can also be between about 0.1 milligrams per kilogram body weight per day and about 20 milligrams per kilogram body weight per day, or between about 1 milligram per kilogram body weight per day and about 10 milligrams per kilogram body weight per day, although other levels or concentrations may be appropriate.

The propylthiouracil-containing pharmaceutical composition administered to the subject in need of inhibition of atherosclerosis or restenosis as described herein can be administered systemically or locally by any route of administration suitable to the particular formulation of the propylthiouracil-containing pharmaceutical composition, the specific nature of the condition to be treated, and the individual subject. Suitable routes of administration include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The propylthiouracil-containing pharmaceutical compositions of the present invention can be administered to the subject by a medical device, when this approach is appropriate to the particular formulation, route of administration, and dosage of the pharmaceutical composition, the specific nature of the condition to be treated, and the individual subject. Suitable devices include, but are not limited to, catheters, balloons, implantable devices, biodegradable implants, prostheses, grafts, sutures, patches, shunts, or stents. The devices can deliver a pharmaceutical composition of the invention over a relatively short period of time, such as a period of less than one week, or over a relatively long period of time, such as a period of up to about six months. However, periods from about one day to about forty-five days would be typical and a period of about seven to about twenty one days would likely be most typical.

The present invention's method of inhibiting atherosclerosis or restenosis in a subject includes administration to the subject of propylthiouracil in an amount sufficient to inhibit vascular smooth muscle cell proliferation in the subject. Preferably, this amount is sufficient to inhibit vascular smooth muscle cell proliferation but not substantially inhibit endothelial cell proliferation in the subject. Also preferably, this amount is sufficient to inhibit vascular smooth muscle cell proliferation but not substantially cause vascular smooth muscle cell cytotoxicity or vascular smooth muscle cell apoptosis in said subject. The amount of propylthiouracil administered to the subject can be an amount sufficient to decrease collagen expression in vascular tissue in the subject. The amount of propylthiouracil administered to the subject can also be an amount sufficient to promote conversion of vascular smooth muscle cells from a non-contractile phenotype to a contractile phenotype in the subject. The amount of propylthiouracil administered to the subject can further be an amount sufficient to inhibit migration activity of vascular smooth muscle cells in the subject.

III. Medical Device with Propylthiouracil

The present invention also provides an article of manufacture including a medical device and propylthiouracil.

Medical Device

The medical device of the present invention's article of manufacture can be any medical device, the use of which can benefit from the inhibition of vascular smooth muscle cell proliferation. Examples of such medical devices include, but are not limited to, catheters, balloons, implantable devices, biodegradable implants, prostheses, grafts, sutures, patches, shunts, or stents. Prostheses include, for example, prosthetic valves, prosthetic vessels, and prosthetic hearts.

The choice of the appropriate medical device may depend in part on the physical condition of the patient as well as the location of the target vascular smooth muscle cell. Medical devices that are less invasive and deliver a pharmaceutical to its target would tend to be preferable.

Coated stents are commonly used within the art of vascular treatment methodologies and provide useful techniques and guidelines for production of medical devices incorporating propylthiouracil and methods of use. For example, stents coated with sirolimus have been successful in clinical trials (Sousa et al., American Heart Association Scientific Sessions, Nov. 11–14, 2001, Anaheim Abstract 115154) and provide generally approaches that are applicable to treatment with propylthiouracil. Stents have also been shown useful in the delivery of pharmaceuticals in U.S. Publication Nos. U.S. Ser. No. 2002/0007213, U.S. Ser. No. 2002/0007214, U.S. Ser. No. 2002/0007215 and U.S. Ser. No. 2002/0016625 and International Publication Nos. WO 01/87374 and WO 01/87376 by Falotico et al.

Alternative drug delivery systems have also been shown useful in the application of pharmaceuticals or medicaments and the like for cardiovascular treatment and would be useful in the application of propylthiouracil. International Patent No. WO 99/21908 by Jackson et al. discloses a polymeric drug delivery system useful as an implantable solid device or as an injectable liquid that solidifies in vivo that is a liquid or paste at 25° C. including a biodegradable water insoluble polymer that is a solid or wax at 37° C., a biodegradable water soluble polymer that is a liquid at 25° C. and a hydrophobic drug. Alternatively, U.S. Publication Ser. Nos. U.S. Ser. No. 2002/0082677, U.S. Ser. No. 2002/0082678 and U.S. Ser. No. 202/0114823 by Sirhan et al. disclose an implantable device with an expansive structure and means on or within the structure for releasing a drug into the vascular system to prevent smooth muscle cell proliferation. International Publication No. WO 00/40278 by Machan et al. discloses stent grafts, compositions for coating stent grafts, as well as methods for making and using these stent grafts to increase or accelerate adherence of the stent graft to the vessel wall.

Balloon angioplasty medical devices that include propylthiouracil may also be preferred. Stents and balloon angioplasty medical devices can also be used to confirm and test the effectiveness of propylthiouracil in mammalian models such as rabbits, monkeys, pigs and dogs. Inserting a stent in the femoral artery of such a test animal would be preferable to the aortic artery because of the heightened probability of recovery from surgery and the relative ease of the procedure.

Coating or Impregnation

Propylthiouracil is provided on or within the medical device of the present invention's article of manufacture. Examples of suitable methods of providing propylthiouracil on or within the medical device of the present invention's article of manufacture include, but are not limited to, providing propylthiouracil as a coating, membrane, film, impregnated matrix, polymer, sponge, gel, or porous layer on or within the medical device.

One factor in selecting the method of providing propylthiouracil on or within the medical device of the present invention's article of manufacture is the length of time over which it is desired to release propylthiouracil from the medical device. Propylthiouracil can be released from the medical device over a relatively short period of time, such as a period of less than one week, or over a relatively long period of time, such as a period of up to about six months when the medical device is provided to or within the subject. U.S. Pat. No. 5,788,979 by Alt et al. discloses a useful method for coating a stent or biomaterial with an anticoagulant to prevent or reduce adherence of blood components to the surface of the stent or biomaterial thereby prolonging its usefulness and would likely be useful in the prolonged release of propylthiouracil. When coating a medical device with propylthiouracil, it may be also be desirable to coat the stent with an antibiotic. Antibiotics have been used in the coating of stents to prevent infection such as in International Publication No. WO 96/29071 by Sivron.

Dose

The article of manufacture of the present invention provides propylthiouracil in an amount sufficient to achieve appropriate serum levels or appropriate localized levels to obtain the desired effect. Such levels or concentrations can be of between about 1 microgram per milliliter and about 10 micrograms per milliliter, or between about 3 microgram per milliliter and about 7 micrograms per milliliter in the subject, or localized serum levels between about 100 micrograms per milliliter and about 1,000 micrograms per milliliter, although other concentrations or levels can be appropriate, particularly depending on the organism, condition, medical procedure or desired outcome. Expressed as a daily dose, this amount can be between about 0.1 milligrams per kilogram body weight per day and about 20 milligrams per kilogram body weight per day, or between about 1 milligrams per kilogram body weight per day and about 10 milligrams per kilogram body weight per day. However one skilled in the art would recognize the dose may vary from species to species, individual to individual or for the medical procedure or device being used. As discussed herein, the appropriate dose can be confirmed using acceptable animal models and clinical trials as is known in the arts, particularly those of pharmacology and surgery.

Activity and Endpoints

The article of manufacture of the present invention provides propylthiouracil in an amount sufficient to inhibit vascular smooth muscle cell proliferation in the subject. Preferably, this amount is sufficient to inhibit vascular smooth muscle cell proliferation but not substantially inhibit endothelial cell proliferation in the subject. Also preferably, this amount is sufficient to inhibit vascular smooth muscle cell proliferation but not substantially cause vascular smooth muscle cell cytotoxicity or vascular smooth muscle cell apoptosis in the subject. The amount of propylthiouracil administered to the subject can be an amount sufficient to decrease collagen expression in vascular tissue in the subject. The amount of propylthiouracil administered to the subject can also be an amount sufficient to promote conversion of vascular smooth muscle cells from a non-contractile phenotype to a contractile phenotype in the subject. The amount of propylthiouracil administered to the subject can further be an amount sufficient to inhibit migration activity of vascular smooth muscle cells in the subject.

As discussed herein, there are a variety of medical procedures that can take advantage of the materials and methods of the present invention. In particular, the present invention finds utility in the field of cardiology, particularly surgery and treatment. The medical devices and pharmaceutical compositions of the present invention can be used alone or in combination. For example, balloon angioplasty medical devices and can include PTU for localized modulation of PTU, as can pharmaceutical compositions aimed at a more systemic modulation of PTU. Thus, a physician tending to a subject, such as a human, scheduled to undergo angioplasty and possible stent insertion has clinical options. The subject can be administered a pharmaceutical composition of the present invention before, during, after, or a combination thereof) such a procedure to modulate systemic PTU concentrations. The balloon angioplasty structure can optionally include PTU to locally modulate PTU concentrations for the short term to the locus of the procedure. Likewise, the stent can optionally include PTU to locally modulate PTU concentrations for longer periods of time after the stent is in place.

Determining and confirming the particular dose, regime, route of administration and coating or impregnation methods and release is within the skill of the artisan of pharmacology and surgery and depends on a variety of factors, such as the species and condition of the subject, the procedure to be followed, the end result desired and the like. Such procedures can first be tested using appropriate models, such as those set forth herein, particularly the ex vivo and animal models set forth herein. The results obtained from these studies can be extrapolated for use in clinical trials and confirmed there, as is routine in the pharmaceutical arts.

By way of example, a rabbit model can be used to determine the efficacy of a particular treatment for balloon angioplasty followed by stent insertion. Of course, a variety of protocols can be envisioned based on the following example. Rabbits that have been over-fed cholesterol tend to have blocked arteries as shown in the Examples herein. Other appropriate test animals can be used in place of rabbits, such as but not limited to monkeys, pigs or dogs. Control rabbits would not be over-fed cholesterol. Both groups could be used, and cholesterol over-fed rabbits at various stages of development or health could be evaluated. Such rabbits can optionally be administered PTU at a variety of concentrations prior to or during the procedure(s). The rabbits can then undergo balloon angioplasty at an appropriate location, such as femoral artery, using balloon angioplasty medical devices having a variety of concentrations of PTU using a variety of coatings. A portion of that population can be monitored for desired results using the methods described herein. Another portion of that population can have untreated stents and stents having PTU inserted at the locus of balloon angioplasty and/or other loci. Alternatively, such stents can be inserted in animals not having undergone balloon angioplasty treatment. A portion of that population can be monitored for desired results using the methods described herein. Another portion of that population can be administered PTU after the procedures and monitored for desired, results using, the methods described herein.

The results of these studies can be extrapolated to formulate human clinical trials as is routine in the art. Such human clinical trials can be used for confirm the protocols, including dose, route of administration, regime, outcome or clinical endpoints.

EXAMPLES

Example 1

Effects of Propylthiouracil on Rabbits on a High Cholesterol Diet

The following example describes the effects of propylthiouracil on the physiology, blood clinical chemistry, and histopathology of rabbits on a high cholesterol diet.

An atherogenic diet such as 2% cholesterol in the diet has been reported to lead to hypercholesterolemia, which promotes atherogenesis in both man and experimental animals (Ross, 1999, *N. Engl. J. Med.*, 340:115; Gross, in "Animal Models in Cardiovascular Research", 2nd ed., Gross (ed.), Kluwer Academic Publishers, London, 1994, pp. 463–474). Therefore, the high cholesterol diet-fed animal is a useful animal model in studying atherosclerotic changes induced by hypercholesterolemia.

Figure 2:
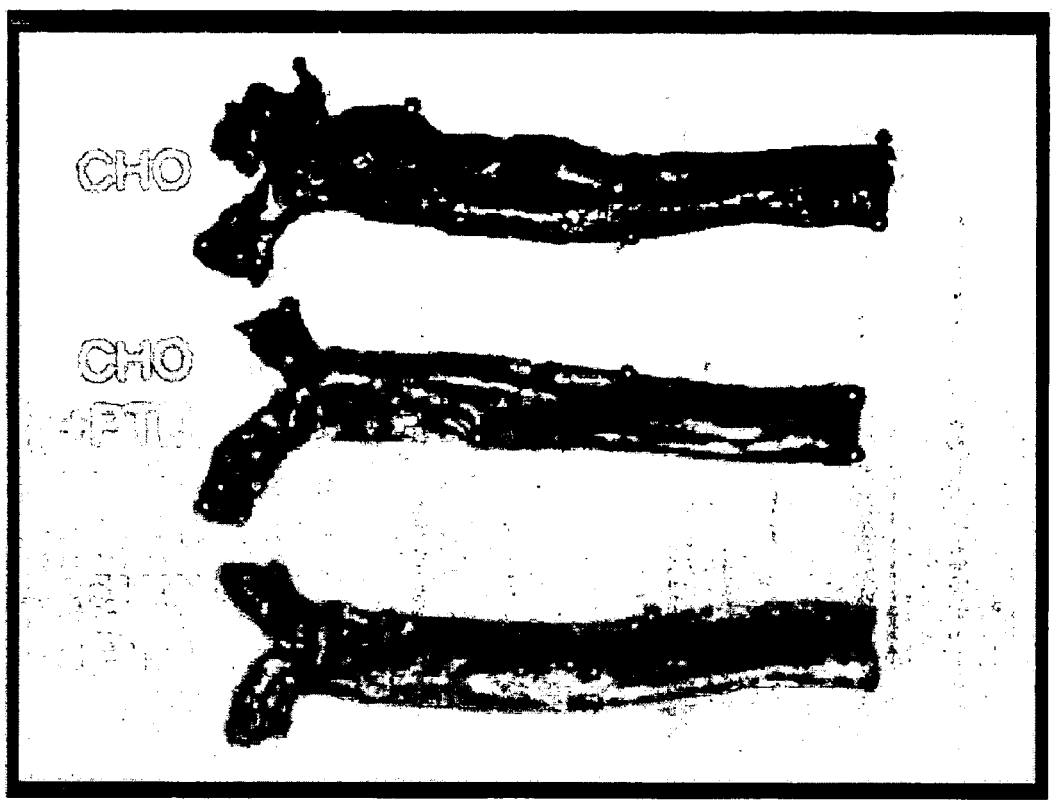
FIG. 2 depicts representative illustration of the sudanophilia distribution in the aortas of three cholesterol-fed rabbits assigned randomly to groups receiving either cholesterol (CHO) alone, cholesterol/propylthiouracil (CHO+PTU), or cholesterol/propylthiouracil/ triiodothyronine hormone (CHO+PTU+$T_3$) as described in Example 1. The presence of 2% cholesterol in the diet resulted in the formation of grossly visible, yellow, atheromatous lesions seen predominantly in the aortic arch and the thoracic aorta. The extent of sudanophilic areas was markedly less in cholesterol/PTU treated rabbits (CHO+PTU) than in the untreated rabbits (CHO). In aortas, the protective effect of propylthiouracil (PTU) on atherosclerosis was not observed to be appreciably abrogated by concomitant treatment with triiodothyronine (CHO+PTU+$T_3$).
Figure 3:
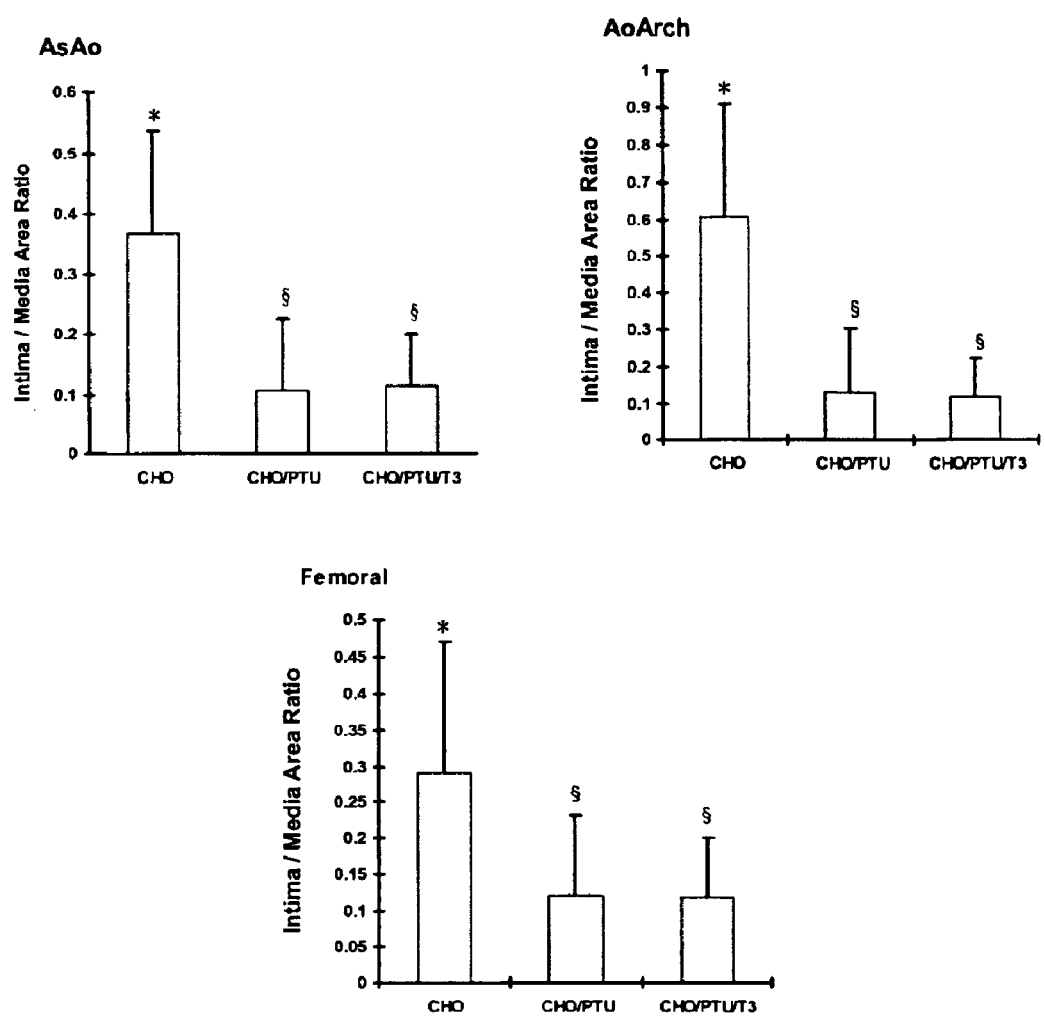
FIG. 3 depicts a quantitative analysis of dietary hypercholesterolemia-induced atherosclerotic lesions determined by measuring intima/media area ratios of the aortic lesions found in cholesterol-fed rabbits assigned randomly to groups receiving either cholesterol (CHO) alone, cholesterol/propylthiouracil (CHO+PTU), or cholesterol/propylthiouracil/triiodothyronine hormone (CHO+PTU+$T_3$) as described in Example 1. Data are expressed separately as ascending aorta (AsAo), aortic arch (AoArch), and femoral arteries (Femoral). $P<0.01$; *, §: different symbols represent significant difference between corresponding groups using Tukey's multiple comparison. The histological features of aortic lesions were comparative between cholesterol (CHO) and cholesterol/PTU-treated rabbits (CHO+PTU). Propylthiouracil (PTU) had a pronounced effect on reducing the severity of aortic atherosclerosis. The extent of aortic atherosclerosis in terms of intima/media area ratio was deceased significantly in the ascending aorta, aortic arch and the femoral arteries.

The present example shows that feeding the rabbits a diet containing 2% cholesterol significantly increased the degree of atherosclerosis present in the aorta and significantly increased the Sudan III-positive lipid in the aorta, with the aortic arch being the most severely affected. The response of the aorta to the 2% cholesterol diet was significantly decreased by concurrent treatment with 0.1% propylthiouracil (Sigma, St. Louis, Mo.) in the drinking water. Exogenous supplement of hypothyroid propylthiouracil-treated rabbits with thyroid hormone could not abrogate the protective effect of propylthiouracil on atherogenesis (FIG. 2 and FIG. 3). The protective effect of propylthiouracil on the genesis of atherosclerosis was a direct effect, not through its hypothyroid effect.

Fifty-seven male New Zealand White rabbits each weighing 2.2–2.5 kilograms were randomly assigned to one of six diet groups: (1) control chow (Control) (Purina Mills, Inc., USA); (2) 0.1% propylthiouracil (Sigma, St. Louis, Mo.) in the drinking water (PTU); (3) 0.1% propylthiouracil in the drinking water plus 15 milligrams of triiodothyronine ($T_3$) (Sigma, St. Louis, Mo.) injected intramuscularly along the hind leg two times per week (PTU+$T_3$); (4) 2% cholesterol diet (catalogue number 57317-9, Purina Mills, Inc, USA); (5) 2% cholesterol diet with 0.1% propylthiouracil in the drinking water (CHO+PTU); or (6) 2% cholesterol diet with 0.1% propylthiouracil in the drinking water plus 15 milligrams of triiodothyronine injected intramuscularly along the hind leg two times per week. The dose of triiodothyronine used was designed to normalize thyroid hormone levels. Body weights, chow, and water consumptions were recorded daily after the experiment. Average daily chow and water consumption are shown in Table 2.

At the end of 12 weeks of study, the rabbits were sacrificed. The aortas (from the ascending aorta to the iliac bifurcation) and femoral arteries were removed, rinsed with phosphate-buffered saline (PBS) and stained with Sudan III, or fixed with 4% paraformaldehyde and paraffin-embedded for hematoxylin-eosin staining or immunohistochemical analysis.

Physiological variables were determined before and at the end of the study. Triplicate measurements of arterial pressure were obtained with an automatic sphygmomanometer in animals lightly anesthetized with xylazine (5 milligrams per kilogram body weight) and ketamine hydrochloride (35 milligrams per kilogram body weight). Heart rates were calculated from the pulse rate averaged over time.

Blood samples were collected every two weeks during the experiment. The pooled sera were used for determining the thyroid hormone index, that is to say, triiodothyronine ($T_3$), thyroxine ($T_4$), and thyrotropin (TSH). Pooled sera were also used for determining serum lipids (serum total cholesterol and serum triglyceride (TG)) and lipoproteins (HDL-cholesterol (Serum HDL), LDL-cholesterol (Serum LDL), and VLDL-cholesterol (Serum VLDL)). The thyroid hormone index was obtained using the Automated Chemiluminescence System (Centaur, Bayer, USA). Lipids and lipoproteins were measured enzymatically with a Hitachi Automatic Analyzer Model 7450 (Hitachi, Japan).

For morphometric studies, up to ten cross sections (5 millimeters thick and 2 millimeters apart from each other) were prepared from each paraffin-embedded segment of the aorta and femoral arteries. The specimens were stained with hematoxylin and eosin. For each cross section of an arterial specimen, the intimal and medial areas were measured. The intima/media area ratio was determined and is shown in FIG. 3.

For immunohistochemical studies, the arterial sections were deparaffinized, rehydrated and blocked in PBS containing 1% bovine serum albumin and 1% goat serum at room temperature for 30 minutes. The sections were then incubated with mouse monoclonal antibodies against smooth muscle cell alpha-actin (clone 1A4, catalogue number M0851, DAKO Corp., Carpenteria, Calif.) and mouse monoclonal antibodies against rabbit macrophages (clone RAM 11, catalogue number M0633, DAKO Corp., Carpenteria, Calif.) at 4° C. overnight. Subsequently, immunohistochemistry was performed using a commercially available peroxidase-labelled streptavidin-biotin kit (DAKO LSAB peroxidase, catalogue number K0675, DAKO, Carpenteria, Calif.) and 3,3'-diaminobenzidine tetrahydrochloride (DAKO liquid DAB+ substrate-chromagen system, catalogue number K3468, DAKO, Carpenteria, Calif.) according to the procedures provide by manufacturer.

Serum propylthiouracil levels were measured by HPLC with mephenoxalone (Tung Yang Chemical Industries, Taiwan) as an internal standard. One hundred microliters of serum was placed into a tube containing 25 microliters of mephenoxalone (Tung Yang Chemical Industries, Taiwan) at 1 milligram per milliliter. All tubes were treated with 25 microliters of 1 molar $K_2HPO_4$ and mixed well by vortexing. The contents of each tube were extracted with 2 milliliters of methyl tert-butyl ether (MTBE) (Sigma, St. Louis, Mo.). Tube contents were mixed and centrifuged for 10 minutes at 3000 rpm at 25° C. The supernatant was transferred to a glass tube, dried under nitrogen gas, and reconstituted with 300 microliters of mobile phase. HPLC was performed by using a Hitachi HPLC system (Hitachi, Japan). An ODS column (Cosmosil 5C18-MS, 4.6 millimeters×250 millimeters, 5 micrometers, Nacalai Tesque, Japan) was used in this chromatographic separation, as well as an ultraviolet detector detecting at 275 nanometers. The mobile phase (acetonitrile/water/phosphoric acid, 40/60/0.5, vol/vol/vol) was degassed and filtered before use. The column flow rate was 1.0 milliliter per minute and column temperature was maintained at 40° C.

cerebral vascular attack, and one in the cholesterol/propylthiouracil/triiodothyronine ($T_3$) group presumably because of poor intake for some unknown reason. At the end of the propylthiouracil treatment, hypothyroid propylthiouracil-treated rabbits (PTU and CHO+PTU) did not have a reduction in the body weight, despite presenting a decrease in water and chow intake. As expected, serum triiodothyronine ($T_3$) and thyroxine ($T_4$) decreased-to unmeasurable levels after 4 weeks treatment with propylthiouracil. Thyrotropin (TSH) level was also found to increase in the hypothyroid groups. This hypothyroid effect could be reversed by a concomitant supplement with triiodothyronine ($T_3$) (FIG. 1A).

TABLE 2

Mean Body Weights, Chow and Water Consumptions, Serum Lipids, Lipoproteins, and Propylthiouracil Levels In Different Treatment Groups of Rabbits
DIET AND TREATMENT

| Number of rabbits (n) | Group 1 (Control) 8 | Group 2 (PTU) 8 | Group 3 (PTU/$T_3$) 8 | Group 4 (CHO) 10 | Group 5 (CHO/PTU) 11 | Group 6 (CHO/PTU/$T_3$) 9 |
|---|---|---|---|---|---|---|
| Chow consumption (grams per day) | 157 ± 15* | 113 ± 13§ | 131 ± 17§ | 156 ± 14* | 123 ± 18§ | 137 ± 13§ |
| Water consumption (milliliters per day) | 336 ± 19* | 196 ± 17§ | 342 ± 67* | 396 ± 49* | 201 ± 41§ | 361 ± 81* |
| Initial weight (kilograms) | 2.46 ± 0.1 | 2.55 ± 0.03 | 2.48 ± 0.08 | 2.41 ± 0.13 | 2.34 ± 0.01 | 2.38 ± 0.11 |
| Weight at sacrifice (kilograms) | 2.7 ± 0.19* | 3.08 ± 0.17§ | 2.51 ± 0.33* | 2.96 ± 0.30 | 3.06 ± 0.17 | 3.05 ± 0.21 |
| Serum CHO at sacrifice (milligrams percent) | 99 ± 11* | 154 ± 22§ | 54 ± 29* | 1926 ± 163 | 1965 ± 156 | 2110 ± 202 |
| Serum TG at sacrifice (milligrams percent) | 61 ± 9* | 175 ± 50§ | 71 ± 12* | 152 ± 84 | 213 ± 167 | 156 ± 93 |
| Serum HDL (milligrams percent) at sacrifice | 43 ± 19 | 43 ± 30 | 29 ± 14 | 45 ± 16 | 67 ± 24 | 61 ± 21 |
| Serum LDL (milligrams percent) at sacrifice | 26 ± 18* | 82 ± 32§ | 23 ± 15* | 1888 ± 190 | 1856 ± 152 | 1998 ± 201 |
| Serum (milligrams percent) at sacrifice | 17 ± 9* | 32 ± 8§ | 14 ± 3* | 30 ± 17 | 43 ± 33 | 31 ± 17 |
| Serum PTU at sacrifice (micrograms per milliliter) | — | 1.57 ± 0.7 | 2.03 ± 1.1 | — | 1.33 ± 1.2 | 1.97 ± 1.1 |

Each value is mean ± SD. PTU = propylthiouracil; CHO = cholesterol; TG = triglyceride; HDL, LDL and VLDL = high, low, and very low density lipoprotein, respectively. *, §: different symbols represent significant difference between corresponding groups using Tukey's multiple comparison.

Mean and standard deviation (SD) were used to describe the data. One-way ANOVA with Tukey's multiple comparison was used to compare continuous data among groups. All p-values presented were 2-sided and the significance level was set to 0.05.

Table 2 compares the values of the 54 rabbits in six groups, each group given a different diet/drug combination. Three animals did not complete the study period. Two animals in the cholesterol diet group (CHO) died because of Referring to Table 2, plasma lipid levels, especially serum cholesterol levels, rose rapidly after high-cholesterol feeding. There was no significant difference in cholesterol, triglyceride, and lipoprotein levels among the three groups (Groups 4–6) fed a high cholesterol diet. However, compared with the control group, rabbits that consumed propylthiouracil only (Group 2) showed a slight increase in serum cholesterol, triglyceride, LDL, and VLDL levels.

The blood counts remained essentially unchanged in the propylthiouracil-treated groups. Agranulocytosis did not occur. In addition, the hypothyroid propylthiouracil-treated groups did not have their arterial pressures and heart rates altered.

Figure 4:
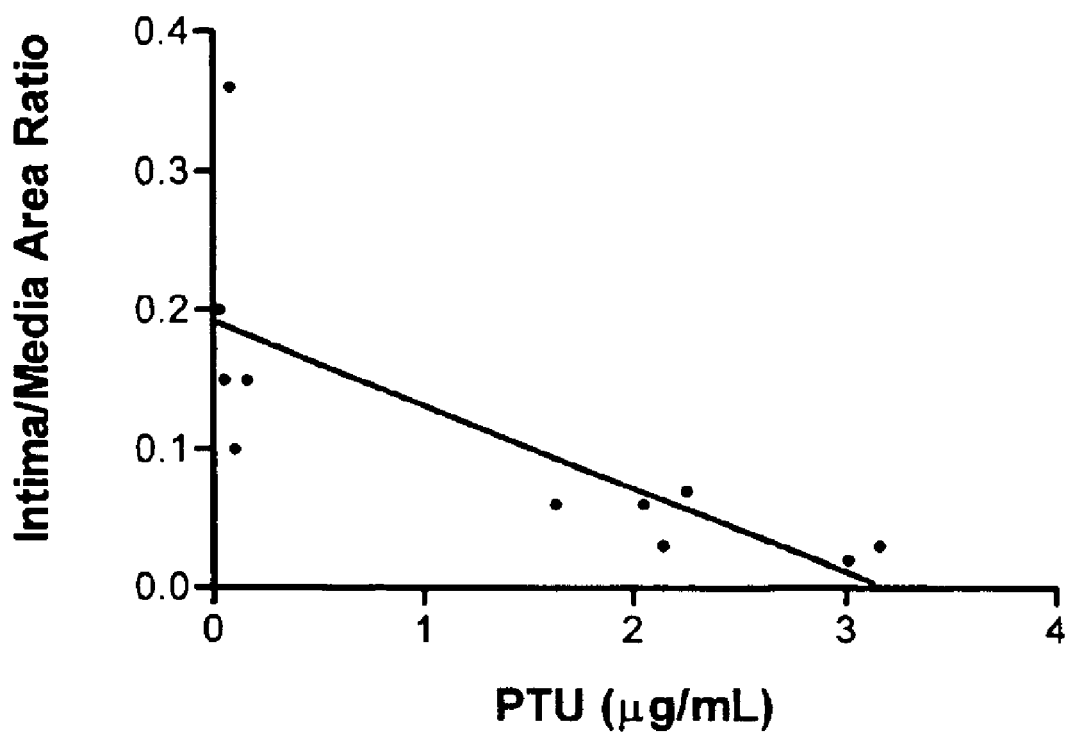
FIG. 4 depicts the relationship between intima/media area ratio and serum propylthiouracil levels in 11 cholesterol-fed/propylthiouracil-treated rabbits (CHO+PTU) as described in Example 1. Intima/media area ratio was inversely related to serum propylthiouracil levels ($P<0.01$, $r=-0.757$) demonstrating an inverse relationship between levels of serum propylthiouracil (PTU) and the severity of atherosclerosis.

FIG. 2 shows representative examples of fatty-streak distribution in the aortas of cholesterol- and of propylthiouracil/cholesterol-treated rabbits [. The presence of 2% cholesterol in the diet resulted in the formation of grossly visible, yellow, atheromatous lesions seen predominantly in the aortic arch and the thoracic aorta. The extent of sudanophilic areas was markedly less in propylthiouracil/cholesterol-treated rabbits. In aortas, the protective effect of propylthiouracil on atherosclerosis could not be abrogated by concomitant treatment with triiodothyronine ($T_3$). The histological features of aortic lesions were comparative between cholesterol (CHO) and propylthiouracil/cholesterol-treated rabbits (CHO+PTU). Propylthiouracil had a pronounced effect on reducing the severity of aortic atherosclerosis. The extent of aortic atherosclerosis in terms of intima/media area ratio was deceased significantly in the ascending aorta, aortic arch and the femoral arteries (FIG. 3). There was an inverse relationship between levels of serum propylthiouracil and intima/media area ratio (FIG. 4). Furthermore, rabbits treated with propylthiouracil only (Groups 2 and 3) had no visible atherosclerotic lesion in their aortas and arteries (data not shown). The absolute area of the media did not differ significantly among the six groups.

Figure 5:
FIG. 5 depicts microscopic localization of rabbit vascular smooth muscle cells (A, C) and macrophages (B, D) in the atheromas of cholesterol-fed (CHO) and cholesterol-fed/propylthiouracil-treated (CHO+PTU) groups (magnification of objective lens, X100) as described in Example 1. Rabbits in the CHO+PTU group had markedly fewer alpha-smooth muscle actin-positive cells than those in the CHO alone group. In addition, decreased number of vascular smooth muscle cells exceeded the decrease in macrophage cells which resulted in a decreased vascular smooth muscle cells/macrophage ratio. Therefore, propylthiouracil (PTU) treatment resulted in a decrease in the number of vascular smooth muscle cells in the atheromas of cholesterol-fed rabbits.
Figure 5:
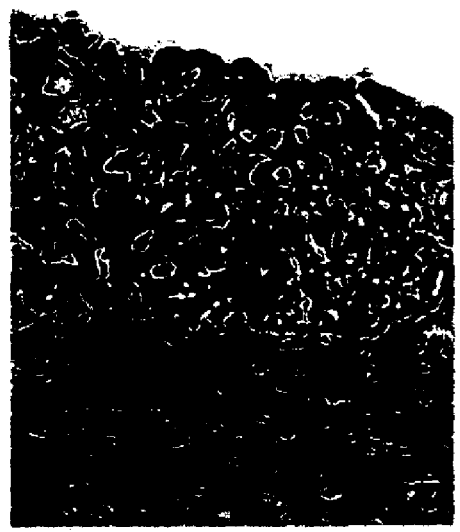
Figure 5:
Figure 5:

In the cholesterol-fed rabbits, the intimal plaques contained large numbers of vascular smooth muscle cells (VSMCs) (FIG. 5, Panel A) and macrophage-derived foam cells (FIG. 5, Panel B). The intimal lesions of the cholesterol-fed rabbits that received 0.1% propylthiouracil in the drinking water (FIG. 5, Panel C) had fewer VSMCs than did the lesions of rabbits receiving cholesterol alone (FIG. 5, Panel A). Rabbits in the propylthiouracil/cholesterol-treated group had significantly fewer alpha-smooth muscle actin-positive cells than those in the cholesterol-treated group (FIG. 5). Overall, propylthiouracil could reduce the VSMC/macrophage ratio in the atherosclerotic lesions induced by high cholesterol diet.

Example 2

Effects of Propylthiouracil of Vascular Cell Proliferation

The following example demonstrates propylthiouracil can selectively inhibit the proliferation of vascular smooth muscle cells and does not significantly inhibit vascular endothelial cell proliferation.

Rat vascular smooth muscle cells (VSMCs) (passages 5–10) were prepared from Sprague-Dawley rats and cultured in Dulbecco's modified Eagle's medium (DMEM) supplemented with 10% fetal bovine serum (FBS) as previously described (Kirschenlohr et al, in "Human Cell Culture Protocols", New Jersey, Humana Press Inc, 1996, pp. 318–335). Human endothelial cells from umbilical veins were prepared as described (Morgan, in "Human Cell Culture Protocols", New Jersey, Humana Press Inc, 1996, pp. 101–152)

Rat vascular smooth muscle cells and human endothelial cells were plated at a density of 10,000 cells per square centimeter in 24-well plates. After 24 hours, cells at 70–80% confluency were treated with propylthiouracil dissolved in 100% dimethylsulfoxide (DMSO) at final concentrations of from 0.05 millimolar to 15 millimolar, or with methimazole (Sigma, St. Louis, Mo.) dissolved in water at the concentrations of from 0.01 millimolar to 1 millimolar for 24–72 hours. Cell numbers were visually counted using a hemocytometer. For the thymidine incorporation study, cells were deprived of serum for 36 hours and labeled with [methyl-$^3$H]thymidine at 1 millicurie per milliliter for 12–24 hours after synchronization. Thymidine incorporation was then measured (Newby and George, 1996, Curr. Opin. Cardiol., 11:547). Effects of propylthiouracil and methimazole on the number of vascular smooth muscle cells and human endothelial cells and thymidine incorporation by vascular smooth muscle cells were each expressed as a percentage of the number and thymidine incorporation of control cells maintained in medium containing 0.1% DMSO as vehicle.

Mean and standard deviation (SD) were used to describe the data. One-way ANOVA with Tukey's multiple comparison was used to compare continuous data among groups. All p-values presented were 2-sided and the significance level was set to 0.05.

Propylthiouracil, but not methimazole, significantly inhibited the proliferation of VSMCs (FIG. 6A) and thymidine incorporation into VSMCs (FIG. 6B) in a concentration-dependent manner. Propylthiouracil decreased the cell number of VSMCs to 103, 103, 76, and 57% of control and inhibited thymidine incorporation into VSMCs to 99, 93, 75, and 38% of control at final concentrations of 0.05, 0.5, 2.5, and 5 millimolar, respectively. Differences between control medium containing 0.1% DMSO and DMSO-free medium were not statistically significant.

In contrast and referring to FIG. 7, treatment for 24 hours with propylthiouracil at concentrations of up to 7.5 millimolar did not significantly inhibit the growth of vascular endothelial cells. A concentration-dependent, significant inhibition of growth of vascular endothelial cells was observed only at concentrations of 10 millimolar or greater ($IC_{50}$ at 5.8 millimolar for VSMCs and $IC_{50}$ at 12 millimolar for endothelial cells).

Figure 8:
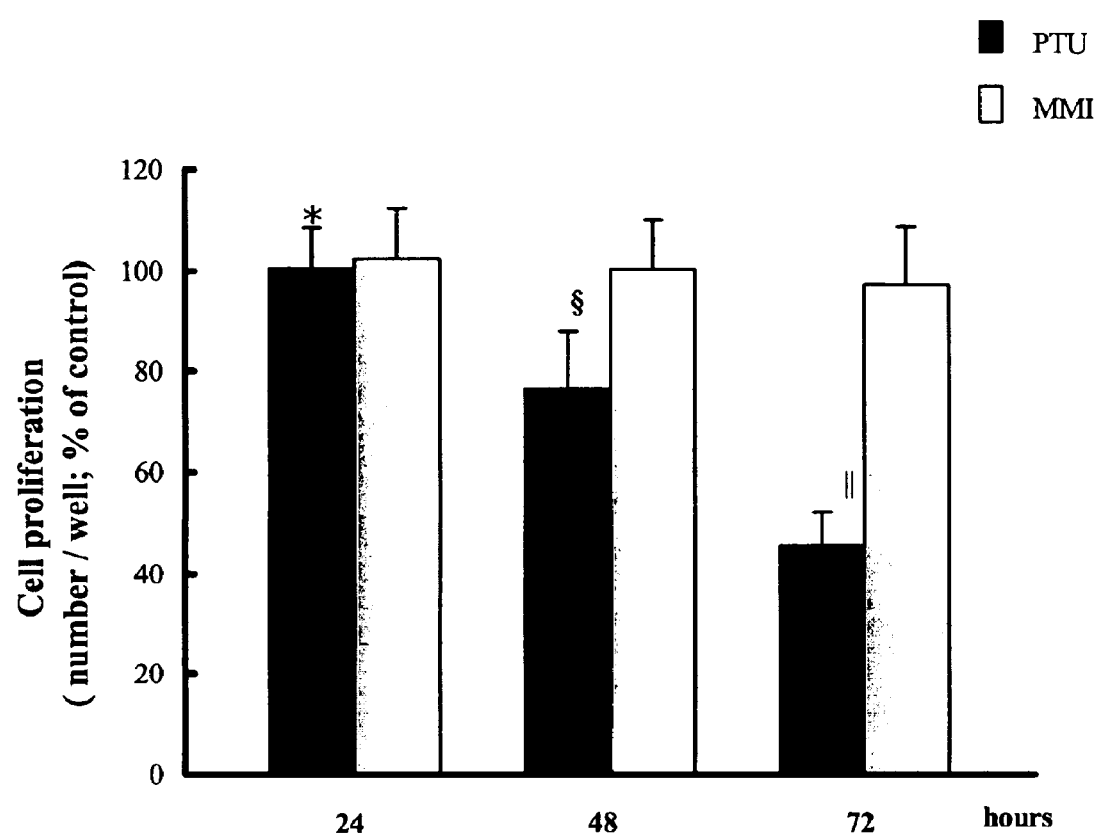
FIG. 8 depicts the long-term effects of low concentrations of propylthiouracil (PTU, 0.05 millimolar) and methimazole (MMI, 0.5 millimolar) on the cell number of rat vascular smooth muscle cells prepared according to Example 2, expressed as a percentage of the number of control cells maintained in medium containing 0.1% DMSO as vehicle. Each value is a mean±SD ($n=6$). $P<0.01$; *, §, ∥: different symbols represent significant difference between propylthiouracil (PTU) groups using Tukey's multiple comparison. The inhibitory effects of propylthiouracil (PTU) treatment for 24 hours on the proliferation of VSMCs were observed at higher concentrations than the physiological concentrations of propylthiouracil (PTU) in clinical usage (1 to 10 $\mu$g/mL). Therefore, the long-term effects of propylthiouracil (PTU) on the proliferation of VSMCs grown at the physiological concentration were investigated. Although the proliferation of VSMCs after 24 hours treatment was not inhibited by the lower concentration of propylthiouracil (PTU) (0.05 millimolar/L≈8.5 $\mu$g/mL), the antiproliferative effect was observed when the cells were exposed to this concentration of propylthiouracil (PTU) for more than 2 days.

The inhibitory effects of propylthiouracil treatment for 24 hours on the proliferation of rat vascular smooth muscle cells were observed at much higher concentrations than the physiological concentrations of propylthiouracil in clinical usage (1 to 10 milligrams per milliliter) (Ferns et al., 1992, Proc. Natl. Acad. Sci., 89:11312). The long-term effects of propylthiouracil at physiological concentrations on the proliferation of VSMCs was also studied. Although the proliferation of VSMCs after 24 hours treatment was not inhibited by the lower concentration of propylthiouracil (0.05 millimolar, equivalent to 8.5 milligrams per milliliter), the antiproliferative effect was indeed observed when the cells were exposed to this concentration of propylthiouracil for more than 2 days (FIG. 8).

Example 3

Absence of Cytotoxic or Apoptotic Effects of Propylthiouracil in Vascular Smooth Muscle Cells.

The following example describes the absence of cytotoxicity or apoptosis in vascular smooth muscle cells due to propylthiouracil treatment.

For determining cytotoxicity, rat vascular smooth muscle cells (VSMCs) were gently trypsinized and their ability to exclude trypan blue was evaluated.

To assess apoptosis, the morphology of propidium iodide (PI)-stained DNA in the cells was examined with the use of fluorescent microscopy. After 24 hours of incubation of VSMCs, cells at 70–80% confluency were treated with or without 5 millimolar propylthiouracil for 24 hours. Cells were fixed with 4% paraformaldehyde, and morphological changes were examined under fluorescent microscope (magnification of objective lens, ×200) after the DNA was stained with propidium iodide. TUNEL (terminal deoxynucleotidyl tranferase (TdT)-mediated dUTP nick end labeling) assays were performed using ApopTag peroxidase kit (Intergen, N.Y., USA). TdT synthesizes fluorescein-labelled dUTP at the 3'-OH ends of the broken DNA strands, which are abundant in apoptotic nuclei.

Propylthiouracil had no cytotoxic effect on vascular smooth muscle cells as assessed by trypan blue exclusion test. After propylthiouracil treatment for 24 hours, the number of cells that excluded trypan blue was 94.4±0.4% compared with 94.2±0.6% in control cells (n=5). Examining of propidium iodide-stained cells showed that propylthiouracil, even at the highest concentration (5 millimolar) tested, did not cause pyknosis or karyorhexis (typical features of apoptosis) in propylthiouracil-treated VSMCs (FIG. 9A) compared with control VSMCs (FIG. 9B). TUNEL-positive cells were absent in propylthiouracil-treated VSMCs as well as in aortas of rabbits from both the propylthiouracil and cholesterol/propylthiouracil treatment groups (EXAMPLE 1), which further shows propylthiouracil's lack of cytotoxicity.

Example 4

Effects of Propylthiouracil on Vascular Smooth Muscle Cell Phenotype

The following example demonstrates propylthiouracil treatment on vascular smooth muscle cells can result in conversion from a non-contractile phenotype to a contractile phenotype.

When cultured in DMEM containing 10% fetal bovine serum (FBS), rat vascular smooth muscle cells (VSMCs) appeared as elongated cells (FIG. 10, Panel A). After the addition of 5 millimolar propylthiouracil into the medium, the cells underwent a striking change to a highly elongated and spindle-shaped cell (FIG. 10, Panel B). These changes were evident after 12 hours and complete by 72 hours. Dose-dependent changes were also observed. Proteins specific to contraction (alpha-actin and calponin) were highly expressed in the contractile state smooth muscle cells. Immunocytochemical staining demonstrated a striking increase in both alpha-actin (FIG. 11A) and calponin (FIG. 11B) formation in VSMCs treated with 5 millimolar propylthiouracil for 24 hours (Panels B and D), relative to control VSMCs (Panels A and C). These results show that propylthiouracil converted vascular smooth muscle cells from a non-contractile phenotype to a fully differentiated contractile phenotype.

Example 5

Effects of Propylthiouracil on Vascular Smooth Muscle Cell Collagen Expression

The following example demonstrates a decrease in collagen I and collagen III expression by vascular smooth cells when treated with propylthiouracil.

Figure 12:
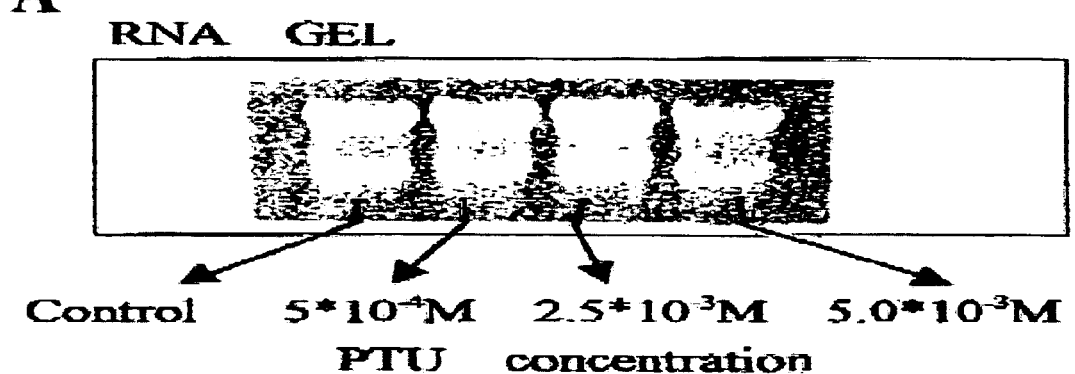
FIG. 12 depicts the effects of propylthiouracil on the expression of pro-α1(I) collagen gene at the RNA level. Northern blot analysis was carried out on total RNA from rat vascular smooth muscle cells grown in media containing 0 (Control), 0.5 millimolar, 2.5 millimolar, or 5 millimolar propylthiouracil and according to Example 5. Pro-alpha-1(I) collagen mRNA radioactivity levels were normalized relative to 18S and 28S rRNA (FIG. 12, Panel A). Propylthiouracil treatment resulted in a concentration-dependent decrease in the abundance of mRNA for pro-alpha-1(I) collagen (Col I) (FIG. 12, Panel B).
Figure 12:
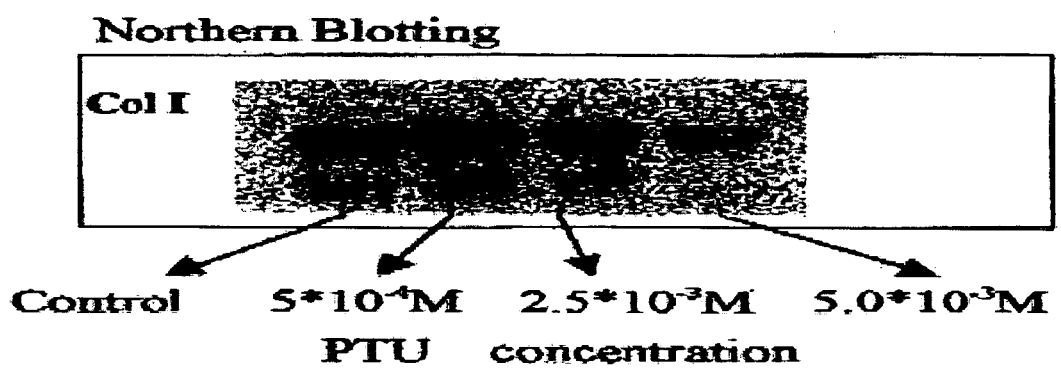

The expression of smooth muscle cell collagen was determined by Northern blot analysis at the RNA level and Western blot analysis on the protein level. Total RNA (10 micrograms) from vascular smooth muscle cells grown in the media containing 0 (Control), 0.5 millimolar, 2.5 millimolar, or 5 millimolar propylthiouracil (PTU) for 24 hours was electrophoresed on a 1% agarose gel. The levels of pro-α1(I) collagen mRNA were measured as radioactivities, normalized relative to the density of 18S and 28S rRNA (FIG. 12, Panel A). Propylthiouracil treatment resulted in a dose-dependent decrease in the abundance of mRNA for pro-alpha-1(I) collagen (Col I) (FIG. 12, Panel B).

Figure 13:
FIG. 13 depicts the effects of lower physiological concentrations of propylthiouracil on the expression of type I and type III collagen genes at the RNA level. Northern blot analysis was carried out on total RNA from rat vascular smooth muscle cells isolated according to Example 2 and grown for 24 to 72 hours (1 to 3 days) in media containing 0 (Control, C), 0.38 millimolar, 0.5 millimolar, or 0.76 millimolar propylthiouracil according to Example 5. Type I collagen (FIG. 13, Panel A) and type III collagen (FIG. 13, Panel B) mRNA radioactivity levels were normalized relative to 18S and 28S rRNA (FIG. 13, Panel C). Propylthiouracil treatment resulted in a concentration-dependent decrease in the abundance of mRNA for both type I and type III collagen.
Figure 13:
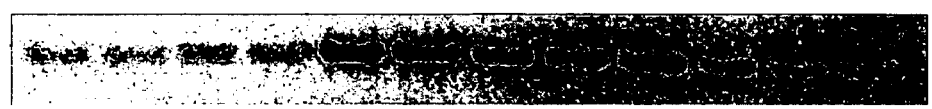
Figure 13:
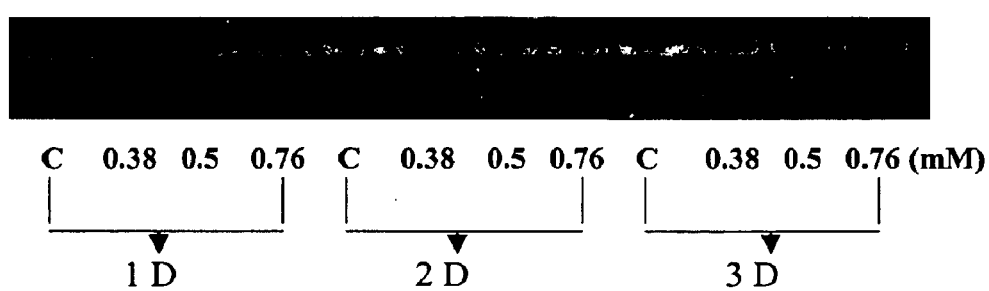
Figure 14:
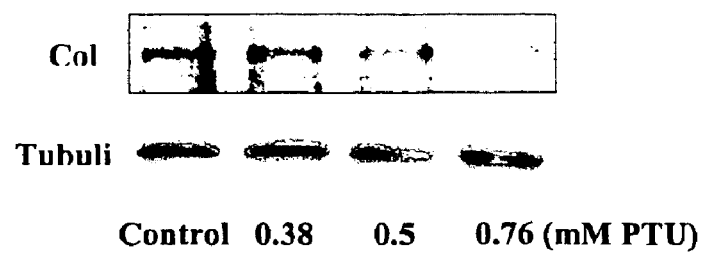
FIG. 14 depicts the effects of lower physiological concentrations of propylthiouracil on the expression of pro-alpha-1(I) collagen gene at the protein level. Western blot analysis was carried out on total protein from vascular smooth muscle cells grown for 72 hours in media containing 0 (Control, C), 0.38 millimolar, 0.5 millimolar, or 0.76 millimolar propylthiouracil according to Example 5. Type I collagen (FIG. 14, Panel A) and type III collagen (FIG. 14, Panel B) protein levels were normalized relative to the protein levels of tubulin. Propylthiouracil treatment resulted in a concentration-dependent decrease in the protein levels of both type I and type III collagen.
Figure 14:
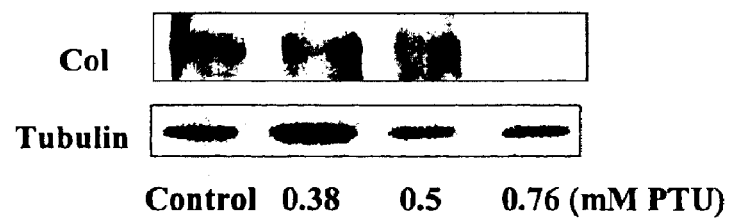
Figure 15A:
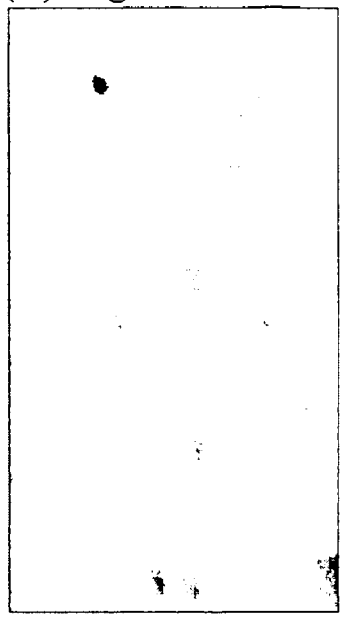
FIG. 15 depicts the effects of propylthiouracil on the expression of type I collagen and type III collagen as demonstrated by immunocytochemistry. Rat vascular smooth muscle cells treated with 0 (Control) or 5 millimolar propylthiouracil (PTU) were stained with antibodies against type I and type III collagen and according to Example 5. Propylthiouracil treatment (FIGS. 15A and 15B, Panel C) resulted in a decrease in the staining density for type I collagen (FIG. 15A) and type III collagen (FIG. 15B), compared to the control cells (Panel B). The negative control included PTU-treated cells without primary antibodies (Panel A).
Figure 15A:
Figure 15A:
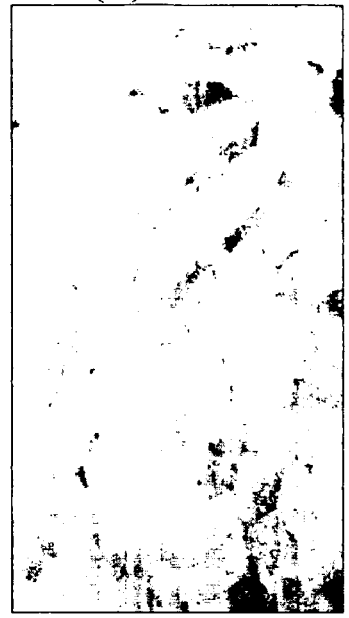
Figure 15B:
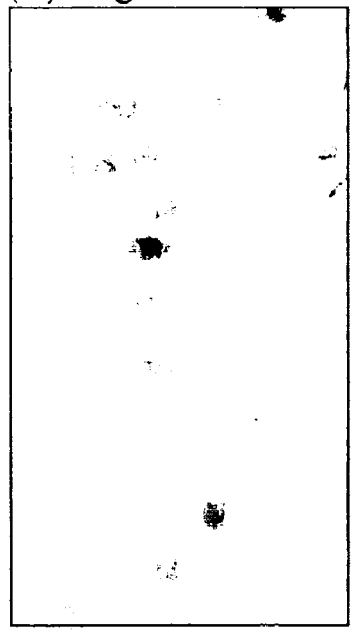
Figure 15B:
Figure 15B:
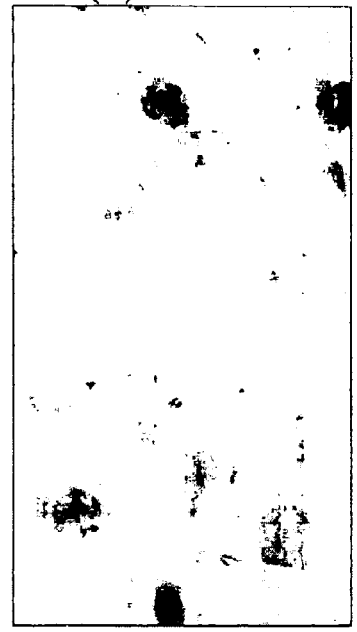

The effects of lower physiological concentrations of propylthiouracil on the expression of type I and type III collagen genes was also studied at the RNA level. Northern blot analysis was carried out on total RNA from rat vascular smooth muscle cells grown for 24 to 72 hours (1 to 3 days) in media containing 0 (Control, C), 0.38 millimolar, 0.5 millimolar, or 0.76 millimolar propylthiouracil. Type I collagen (FIG. 13, Panel A) and type III collagen (FIG. 13, Panel B) mRNA radioactivity levels were normalized relative to 18S and 28S rRNA (FIG. 13, Panel C). Propylthiouracil treatment resulted in a dose-dependent decrease in the abundance of mRNA for both type I and type III collagen.

To measure the effects of lower physiological concentrations of propylthiouracil on the expression of pro-alpha-1(I) collagen gene at the protein level, Western blot analysis was carried out on total protein from vascular smooth muscle cells grown for 72 hours in media containing 0 (Control, C), 0.38 millimolar, 0.5 millimolar, or 0.76 millimolar propylthiouracil. Type I collagen (FIG. 14, Panel A) and type III collagen (FIG. 14, Panel B) protein levels were normalized relative to the protein levels of tubulin. Propylthiouracil treatment resulted in a dose-dependent decrease in the protein levels of both type I and type III collagen.

Immunocytochemistry also demonstrated the effects of propylthiouracil on the expression of type I collagen and type III collagen. Vascular smooth muscle cells treated with 0 (Control) or 5 millimolar propylthiouracil (PTU) were stained with antibodies against type I and type III collagen (Novotec, St Martin La Garenne, France). Propylthiouracil treatment (FIGS. 15A and 15B, Panel C) resulted in a decrease in the staining density for type I collagen (FIG. 15A) and type III collagen (FIG. 15B), compared to the control cells (Panel B). The negative control included PTU-treated cells without primary antibodies (Panel A).

Example 6

Effects of Propylthiouracil on Vascular Smooth Muscle Cell Migration Activity

The following example demonstrates propylthiouracil treatment on vascular smooth cells can inhibit vascular smooth muscle cell migration in a dose-dependent manner.

Vascular smooth muscle cells ($1 \times 10^6$ cells) were added to the apical chamber of transwell culture dishes (Corning, N.Y., USA), incubated for 5 hours, cells that migrated from the apical chamber, through the dividing filter, and into the basal chamber were fixed, stained with Giemsa solution, and counted under the light microscope. Migration activity was expressed as the number of cells in the basal chamber. Each value is a mean±SD (n=5). The results are depicted in FIG. 16, which shows that propylthiouracil inhibited cell migration activity in a dose-dependent manner over the range of concentrations tested.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A method of inhibiting atherosclerosis in a subject, comprising:
   a) identifying a subject suspected of needing inhibition of atherosclerosis; and
   b) administering to said subject PTU in an amount sufficient to inhibit atherosclerosis in said subject,
      wherein said PTU is provided in an amount sufficient not to cause vascular smooth muscle cell apoptosis in said subject.

2. The method of claim 1, wherein said PTU is provided in an amount sufficient to decrease collagen expression in vascular tissue in said subject.

3. The method of claim 1, wherein said PTU is provided in an amount sufficient to promote conversion of vascular smooth muscle cells from a non-contractile phenotype to a contractile phenotype in said subject.

4. The method of claim 1, wherein said PTU is provided in an amount sufficient to inhibit migration activity of vascular smooth muscle cells in said subject.

5. The method of claim 1, wherein said subject is identified by evaluation of said subject's health history, conducting a physical examination, or by performing clinical testing.

6. The method of claim 1, wherein said subject is suspected of having, or has been diagnosed as having atherosclerosis.

7. The method of claim 1, wherein said subject is suspected of having, or has been diagnosed as having atherosclerosis.

8. The method of claim 1, wherein said subject is suspected of having, or has been diagnosed as having coronary artery disease.

9. The method of claim 1, wherein said subject is suspected of having, or has been diagnosed as having a stroke.

10. The method of claim 1, wherein said subject is suspected of having, or has been diagnosed as having restinosis.

11. The method of claim 1, wherein said subject is to undergo vascular surgery.

12. The method of claim 1, wherein said subject is to undergo angioplasty.

13. The method of claim 1, wherein said subject is to undergo balloon angioplasty.

14. The method of claim 1, wherein said subject is to undergo insertion of a prosthesis.

15. The method of claim 1, wherein said subject is to undergo insertion of a graft.

16. The method of claim 1, wherein said subject is to undergo insertion of a stent.

17. The method of claim 1, wherein said subject is to undergo catheterization.

18. The method of claim 1, wherein said subject is to undergo arterial blockage evaluation.

19. The method of claim 1, wherein said subject is a human.

20. The method of claim 1, wherein said PTU is provided in an amount sufficient to achieve serum levels of between about 1 microgram per milliliter and about 10 micrograms per milliliter in said subject.

21. The method of claim 1, wherein said PTU is provided in an amount sufficient to achieve serum levels of between about 3 micrograms per milliliter and about 7 micrograms per milliliter in said subject.

22. The method of claim 1, wherein said PTU is administered to said subject at a dose of between about 0.1 milligrams/kilogram/day and about 20 milligrams/kilogram/day.

23. The method of claim 1, wherein said PTU is administered to said subject at a dose of between about 1 milligrams/kilogram/day and about 10 milligrams/kilogram/day.

24. The method of claim 1, wherein said pharmaceutical composition is administered to said subject by an oral route.

25. The method of claim 1, wherein said pharmaceutical composition is administered to said subject by an intravenous route.

26. The method of claim 1, wherein said pharmaceutical composition is administered to said subject by a parental route.

27. The method of claim 1, wherein said pharmaceutical composition is administered to said subject by an intramuscular route.

28. The method of claim 1, wherein said pharmaceutical composition is administered to said subject by a subcutaneous route.

29. The method of claim 1, wherein said pharmaceutical composition is administered to said subject by a rectal route.

30. The method of claim 1, wherein said pharmaceutical composition is administered to said subject by an intraventricular route.

31. The method of claim 1, wherein said pharmaceutical composition is administered to said subject by an intraatrial route.

32. The method of claim 1, wherein said pharmaceutical composition is administered to said subject by an intraaortal route.

33. The method of claim 1, wherein said pharmaceutical composition is administered to said subject by an intraarterial route.

34. The method of claim 1, wherein said pharmaceutical composition is administered to said subject by an intraperitoneal route.

35. The method of claim 1, wherein said pharmaceutical composition is administered to said subject by a medical device.

36. The method of claim 1, wherein said pharmaceutical composition is administered to said subject by a catheter.

37. The method of claim 1, wherein said pharmaceutical composition is administered to said subject by a balloon.

38. The method of claim 1, wherein said pharmaceutical composition is administered to said subject by an implantable device.

39. The method of claim 1, wherein said pharmaceutical composition is administered to said subject by a prosthesis.

40. The method of claim 1, wherein said pharmaceutical composition is administered to said subject by a graft.

41. The method of claim 1, wherein said pharmaceutical composition is administered to said subject by a stent.

42. A method of inhibiting restinosis in a subject, comprising:
   c) identifying a subject suspected of needing inhibition of restinosis; and
   d) administering to said subject PTU in an amount sufficient to inhibit restinosis in said subject,
      wherein said PTU is provided in an amount sufficient not to substantially cause vascular smooth muscle cell apoptosis in said subject.

43. The method of claim 42, wherein said PTU is provided in an amount sufficient to decrease collagen expression in vascular tissue in said subject.

44. The method of claim 42, wherein said PTU is provided in an amount sufficient to promote conversion of vascular smooth muscle cells from a non-contractile phenotype to a contractile phenotype in said subject.

45. The method of claim 42, wherein said PTU is provided in an amount sufficient to inhibit migration activity of vascular smooth muscle cells in said subject.

46. The method of claim 42, wherein said subject is identified by evaluation of said subject's health history, conducting a physical examination, or by performing clinical testing.

47. The method of claim 42, wherein said subject is suspected of having, or has been diagnosed as having atherosclerosis.

48. The method of claim 42, wherein said subject is suspected of having, or has been diagnosed as having arteriosclerosis.

49. The method of claim 42, wherein said subject is suspected of having, or has been diagnosed as having coronary artery disease.

50. The method of claim 42, wherein said subject is suspected of having, or has been diagnosed as having a stroke.

51. The method of claim 42, wherein said subject is suspected of having, or has been diagnosed as having restinosis.

52. The method of claim 42, wherein said subject is to undergo vascular surgery.

53. The method of claim 42, wherein said subject is to undergo angioplasty.

54. The method of claim 42, wherein said subject is to undergo balloon angioplasty.

55. The method of claim 42, wherein said subject is to undergo insertion of a prosthesis.

56. The method of claim 42, wherein said subject is to undergo insertion of a graft.

57. The method of claim 42, wherein said subject is to undergo insertion of a stent.

58. The method of claim 42, wherein said subject is to undergo catheterization.

59. The method of claim 42, wherein said subject is to undergo arterial blockage evaluation.

60. The method of claim 42, wherein said subject is a human.

61. The method of claim 42, wherein said PTU is provided in an amount sufficient to achieve serum levels of between about 1 microgram per milliliter and about 10 micrograms per milliliter in said subject.

62. The method of claim 42, wherein said PTU is provided in an amount sufficient to achieve serum levels of between about 3 micrograms per milliliter and about 7 micrograms per milliliter in said subject.

63. The method of claim 42, wherein said PTU is administered to said subject at a dose of between about 0.1 milligrams/kilogram/day and about 20 milligrams/kilogram/day.

64. The method of claim 42, wherein said PTU is administered to said subject at a dose of between about 1 milligrams/kilogram/day and about 10 milligrams/kilogram/day.

65. The method of claim 42, wherein said pharmaceutical composition is administered to said subject by an oral route.

66. The method of claim 42, wherein said pharmaceutical composition is administered to said subject by an intravenous route.

67. The method of claim 42, wherein said pharmaceutical composition is administered to said subject by a parental route.

68. The method of claim 42, wherein said pharmaceutical composition is administered to said subject by an intramuscular route.

69. The method of claim 42, wherein said pharmaceutical composition is administered to said subject by a subcutaneous route.

70. The method of claim 42, wherein said pharmaceutical composition is administered to said subject by a rectal route.

71. The method of claim 42, wherein said pharmaceutical composition is administered to said subject by an intraventricular route.

72. The method of claim 42, wherein said pharmaceutical composition is administered to said subject by an intraatrial route.

73. The method of claim 42, wherein said pharmaceutical composition is administered to said subject by an intraaortal route.

74. The method of claim 42, wherein said pharmaceutical composition is administered to said subject by an intraarterial route.

75. The method of claim 42, wherein said pharmaceutical composition is administered to said subject by an intraperitoneal route.

76. The method of claim 42, wherein said pharmaceutical composition is administered to said subject by a medical device.

77. The method of claim 42, wherein said pharmaceutical composition is administered to said subject by a catheter.

78. The method of claim 42, wherein said pharmaceutical composition is administered to said subject by a balloon.

79. The method of claim 42, wherein said pharmaceutical composition is administered to said subject by an implantable device.

80. The method of claim 42, wherein said pharmaceutical composition is administered to said subject by a prosthesis.

81. The method of claim 42, wherein said pharmaceutical composition is administered to said subject by a graft.

82. The method of claim 42, wherein said pharmaceutical composition is administered to said subject by a stent.

* * * * *